(12) United States Patent
Anderson et al.

(10) Patent No.: US 6,867,051 B1
(45) Date of Patent: Mar. 15, 2005

(54) POINT OF CARE DIAGNOSTIC SYSTEMS

(75) Inventors: Emory V. Anderson, Danville, CA (US); Jerome Lapointe, Oakland, CA (US); Ricardo Martinez, Santa Cruz, CA (US); Gail Marzolf, Cupertino, CA (US); Ronald Pong, San Jose, CA (US); Lynn Jones, Mountainview, CA (US); Robert O. Hussa, Sunnyvale, CA (US); Edward Nemec, Duluth, GA (US); Andrew E. Senyei, La Jolla, CA (US); Duane DeSieno, La Jolla, CA (US)

(73) Assignee: Adeza Biomedical, Inc., Sunnyvale, CA (US)

( * ) Notice: Subject to any disclaimer, the term of this patent is extended or adjusted under 35 U.S.C. 154(b) by 20 days.

(21) Appl. No.: 09/717,478

(22) Filed: Nov. 20, 2000

Related U.S. Application Data

(60) Division of application No. 09/063,497, filed on Apr. 20, 1998, now Pat. No. 6,394,952, and a continuation-in-part of application No. 09/017,901, filed on Feb. 3, 1998, now Pat. No. 6,267,722.

(51) Int. Cl.[7] ............................................ G01N 33/543
(52) U.S. Cl. ....................... 436/518; 436/518; 435/7.1; 435/7.21; 422/56; 422/82.09; 356/446; 250/461; 385/116
(58) Field of Search ........................ 436/518; 435/7.21; 435/7.1; 422/82.04, 56; 385/116; 250/339, 461; 128/665; 356/446

(56) References Cited

U.S. PATENT DOCUMENTS

| | | |
|---|---|---|
| 3,600,099 A | 8/1971 | Schoeffel .................... 356/206 |
| 3,734,630 A | 5/1973 | McIntosh et al. ........... 356/203 |
| 3,762,817 A | 10/1973 | Harklau ....................... 356/73 |
| 3,905,767 A | 9/1975 | Morris et al. ............. 23/230 B |
| 3,924,948 A | 12/1975 | Thoden et al. ................ 356/71 |
| 4,160,008 A | 7/1979 | Fenocketti et al. ........... 422/56 |
| 4,160,646 A | 7/1979 | Furutani et al. .......... 23/230 R |
| 4,197,088 A | 4/1980 | Meserol et al. ........... 23/230 B |
| 4,225,575 A | 9/1980 | Piasio et al. .................... 424/1 |
| 4,264,560 A | 4/1981 | Natelson |
| 4,267,261 A | 5/1981 | Hallman et al. ............ 430/322 |
| 4,268,173 A | 5/1981 | Barnard et al. ............. 356/445 |
| 4,366,241 A | 12/1982 | Tom et al. ...................... 435/7 |

(List continued on next page.)

FOREIGN PATENT DOCUMENTS

| | | |
|---|---|---|
| CA | 1305921 | 8/1992 |
| CA | 1339117 | 7/1997 |
| EP | 0387630 | 9/1990 |

(List continued on next page.)

OTHER PUBLICATIONS

Certified English Translation of JP 4130247 (Item No. D).
Certified English Translation of JP 9119894 (Item No. J).

(List continued on next page.)

*Primary Examiner*—Long V. Le
*Assistant Examiner*—Deborah A Davis
(74) *Attorney, Agent, or Firm*—Fish & Richardson P.C.; Stephanie L. Seidman

(57) ABSTRACT

Systems and methods for medical diagnosis or risk assessment for a patient are provided. These systems and methods are designed to be employed at the point of care, such as in emergency rooms and operating rooms, or in any situation in which a rapid and accurate result is desired. The systems and methods process patient data, particularly data from point of care diagnostic tests or assays, including immunoassays, electrocardiograms, X-rays and other such tests, and provide an indication of a medical condition or risk or absence thereof. The systems include an instrument for reading or evaluating the test data and software for converting the data into diagnostic or risk assessment information.

30 Claims, 15 Drawing Sheets

U.S. PATENT DOCUMENTS

| | | | |
|---|---|---|---|
| 4,372,682 A | 2/1983 | Nenninger et al. | 356/244 |
| 4,373,932 A | 2/1983 | Gribnau | 436/501 |
| 4,379,224 A | 4/1983 | Engstrom | 235/463 |
| 4,400,353 A | 8/1983 | Meserol et al. | 422/73 |
| 4,436,826 A | 3/1984 | Wang | 436/525 |
| 4,438,327 A | 3/1984 | Smith | 235/462 |
| 4,511,259 A | 4/1985 | Horiuchi | 368/10 |
| 4,523,853 A | 6/1985 | Rosenbladt et al. | 356/446 |
| 4,537,861 A | 8/1985 | Elings et al. | 436/518 |
| 4,552,458 A | 11/1985 | Lowne | 356/446 |
| 4,552,839 A | 11/1985 | Gould et al. | 435/7 |
| 4,637,985 A | 1/1987 | Sidki et al. | 436/518 |
| 4,647,544 A | 3/1987 | Nicoli et al. | 436/518 |
| 4,659,229 A * | 4/1987 | Hernicz | 356/446 |
| 4,666,309 A | 5/1987 | Barry et al. | 356/446 |
| 4,676,653 A | 6/1987 | Strohmeier et al. | 356/446 |
| 4,689,202 A | 8/1987 | Khoja et al. | 422/65 |
| 4,695,554 A | 9/1987 | O'Connell et al. | 436/528 |
| 4,703,017 A | 10/1987 | Campbell et al. | 436/501 |
| 4,716,123 A | 12/1987 | Wood | 436/533 |
| 4,738,823 A | 4/1988 | Engelmann | 422/56 |
| 4,742,011 A | 5/1988 | Blake et al. | 436/518 |
| 4,748,042 A | 5/1988 | Linnecke et al. | 427/2 |
| 4,782,511 A | 11/1988 | Nemec et al. | 379/93 |
| D299,860 S | 2/1989 | Fan et al. | D24/17 |
| 4,803,048 A | 2/1989 | Nason | 422/58 |
| D300,463 S | 3/1989 | Nemec et al. | D24/17 |
| 4,818,677 A | 4/1989 | Hay-Kaufman et al. | 435/4 |
| 4,820,489 A | 4/1989 | Rothe et al. | 422/56 |
| 4,820,491 A | 4/1989 | Khoja et al. | 422/63 |
| 4,826,659 A | 5/1989 | Akisada | 422/63 |
| 4,838,697 A | 6/1989 | Kurandt | 356/406 |
| 4,855,240 A | 8/1989 | Rosenstein et al. | 436/514 |
| 4,857,457 A | 8/1989 | Shamsuddin et al. | 435/7 |
| 4,861,711 A | 8/1989 | Friesen et al. | 436/7 |
| 4,867,946 A | 9/1989 | Gross et al. | 422/68 |
| 4,868,767 A | 9/1989 | Colvin, Jr. et al. | 364/525 |
| 4,874,691 A | 10/1989 | Chandler | 435/7 |
| 4,894,326 A | 1/1990 | Matsuura et al. | 435/7 |
| 4,902,629 A | 2/1990 | Meserol et al. | 436/165 |
| 4,907,857 A | 3/1990 | Giuliani et al. | 350/96.29 |
| 4,916,056 A | 4/1990 | Brown, III et al. | 435/7 |
| 4,918,025 A | 4/1990 | Grenner | 436/165 |
| 4,919,889 A | 4/1990 | Jones et al. | 422/40 |
| 4,920,046 A | 4/1990 | McFarland et al. | 435/7 |
| 4,934,817 A | 6/1990 | Gassenhuber | 356/446 |
| 4,935,346 A | 6/1990 | Phillips et al. | 435/14 |
| 4,943,522 A | 7/1990 | Eisinger et al. | 435/7 |
| 4,945,250 A | 7/1990 | Bowen et al. | 250/461.1 |
| 4,960,691 A | 10/1990 | Gordon et al. | 435/6 |
| 4,962,154 A | 10/1990 | Pollock | 525/54.1 |
| 4,963,324 A * | 10/1990 | May | 422/60 |
| 4,980,298 A | 12/1990 | Blake et al. | 436/518 |
| 4,981,786 A | 1/1991 | Dafforn et al. | 435/7 |
| 5,006,474 A | 4/1991 | Horstman et al. | 436/524 |
| 5,008,080 A | 4/1991 | Brown, III et al. | 422/56 |
| 5,036,479 A | 7/1991 | Prednis et al. | 364/580 |
| 5,047,206 A | 9/1991 | Dombrowski | 422/56 |
| 5,055,261 A | 10/1991 | Khoja et al. | 422/64 |
| 5,059,394 A | 10/1991 | Phillips et al. | 422/68.1 |
| 5,073,342 A | 12/1991 | Porte et al. | 422/64 |
| 5,073,484 A | 12/1991 | Swanson et al. | 435/7.92 |
| 5,075,215 A | 12/1991 | Dreyer | 435/6 |
| 5,079,171 A | 1/1992 | Senyei et al. | 436/510 |
| 5,087,556 A | 2/1992 | Ertinghausen | 435/7.9 |
| 5,094,955 A | 3/1992 | Calandra et al. | 435/291 |
| 5,096,830 A | 3/1992 | Senyei et al. | 436/65 |
| 5,100,805 A | 3/1992 | Ziege et al. | 436/517 |
| 5,104,811 A | 4/1992 | Berger et al. | 436/164 |
| 5,118,183 A | 6/1992 | Cargill et al. | 356/73 |
| 5,120,643 A | 6/1992 | Ching et al. | 435/7.92 |
| 5,120,662 A | 6/1992 | Chan et al. | 436/530 |
| D328,135 S | 7/1992 | Fan et al. | D24/223 |
| 5,130,936 A | 7/1992 | Sheppard et al. | 364/551.01 |
| 5,132,097 A | 7/1992 | Van Deusen et al. | 422/82.09 |
| 5,132,206 A | 7/1992 | Dreyer | 435/6 |
| 5,135,160 A | 8/1992 | Tasaki | 235/462 |
| 5,141,850 A | 8/1992 | Cole et al. | 436/525 |
| 5,143,694 A | 9/1992 | Schafer et al. | 422/65 |
| 5,147,606 A | 9/1992 | Charlton et al. | 422/56 |
| 5,147,609 A | 9/1992 | Grenner | 422/58 |
| 5,149,622 A | 9/1992 | Brown et al. | 435/5 |
| 5,157,733 A | 10/1992 | Takeo et al. | 382/6 |
| 5,160,486 A | 11/1992 | Schlipfenbacher et al. | 422/56 |
| 5,173,261 A | 12/1992 | Krause et al. | 422/58 |
| 5,179,005 A | 1/1993 | Phillips et al. | 435/14 |
| 5,179,288 A | 1/1993 | Miffitt et al. | 250/564 |
| 5,182,216 A | 1/1993 | Clayton et al. | 436/518 |
| 5,185,127 A | 2/1993 | Vonk | 422/56 |
| 5,185,270 A | 2/1993 | Senyei et al. | 436/510 |
| 5,192,856 A | 3/1993 | Schaham | 235/462 |
| 5,198,369 A | 3/1993 | Itoh et al. | 436/534 |
| 5,202,268 A | 4/1993 | Kuhn et al. | 436/525 |
| 5,223,219 A | 6/1993 | Subramanian et al. | 422/55 |
| 5,223,440 A | 6/1993 | Teng et al. | 436/510 |
| 5,227,893 A | 7/1993 | Ett | 358/400 |
| 5,236,846 A | 8/1993 | Senyei et al. | 436/65 |
| 5,243,655 A | 9/1993 | Wang | 380/51 |
| 5,246,858 A | 9/1993 | Arbuckle et al. | 436/8 |
| 5,249,259 A | 9/1993 | Harvey | 395/13 |
| 5,251,626 A | 10/1993 | Nickolls et al. | 607/14 |
| 5,252,459 A | 10/1993 | Tarcha et al. | 435/6 |
| D341,663 S | 11/1993 | Coulter | D24/225 |
| 5,262,625 A | 11/1993 | Tom et al. | 235/462 |
| 5,266,497 A | 11/1993 | Imai et al. | 436/514 |
| D342,575 S | 12/1993 | Ashihara et al. | D24/224 |
| 5,275,785 A | 1/1994 | May et al. | 422/56 |
| 5,281,522 A | 1/1994 | Senyei et al. | 435/7.9 |
| 5,288,648 A | 2/1994 | Pouletty et al. | 436/514 |
| 5,299,284 A | 3/1994 | Roy | 395/22 |
| 5,301,681 A | 4/1994 | DeBan et al. | 128/736 |
| 5,304,468 A | 4/1994 | Phillips et al. | 435/14 |
| 5,304,786 A | 4/1994 | Pavlidis et al. | 235/462 |
| 5,306,622 A | 4/1994 | Mangold | 435/7.92 |
| 5,316,727 A | 5/1994 | Suzuki et al. | 422/68.1 |
| 5,321,492 A | 6/1994 | Detwiler et al. | 356/73 |
| 5,331,550 A | 7/1994 | Stafford et al. | 364/413.02 |
| 5,354,692 A | 10/1994 | Yang et al. | 436/514 |
| 5,392,403 A | 2/1995 | Kaufmann | 395/275 |
| 5,408,535 A | 4/1995 | Howard, III et al. | 382/1 |
| 5,415,994 A | 5/1995 | Imrich et al. | 435/5 |
| 5,424,035 A | 6/1995 | Hones et al. | 422/55 |
| D361,842 S | 8/1995 | Nazareth et al. | D24/225 |
| 5,455,890 A | 10/1995 | Wang | 395/22 |
| 5,457,313 A | 10/1995 | Baylor et al. | 250/227.21 |
| 5,463,548 A | 10/1995 | Asada et al. | 364/413.02 |
| 5,467,778 A | 11/1995 | Catt et al. | 128/738 |
| 5,468,619 A | 11/1995 | Senyei et al. | 435/7.94 |
| 5,473,537 A | 12/1995 | Glazer et al. | 364/419.2 |
| 5,481,481 A | 1/1996 | Frey et al. | 364/551.01 |
| 5,496,702 A | 3/1996 | Bishop et al. | 435/7.39 |
| 5,500,375 A | 3/1996 | Lee-Own et al. | 436/514 |
| D369,868 S | 5/1996 | Nazareth et al. | D24/225 |
| 5,516,702 A | 5/1996 | Senyei et al. | 436/510 |
| 5,526,120 A | 6/1996 | Jina et al. | 356/446 |
| 5,537,590 A | 7/1996 | Amado | 395/600 |
| 5,544,308 A | 8/1996 | Giordano et al. | 395/183.02 |
| 5,563,042 A | 10/1996 | Phillips et al. | 435/14 |
| D375,799 S | 11/1996 | Leiva et al. | D24/224 |
| 5,578,306 A | 11/1996 | Lessey | 424/143.1 |
| 5,580,794 A | 12/1996 | Allen | 436/169 |

| | | | |
|---|---|---|---|
| 5,585,278 A | 12/1996 | Vunnam et al. | 436/533 |
| 5,590,665 A | 1/1997 | Kanai | 128/898 |
| 5,591,645 A | 1/1997 | Rosenstein | 436/514 |
| 5,594,637 A | 1/1997 | Eisenberg et al. | 395/202 |
| 5,597,532 A | 1/1997 | Connolly | 422/58 |
| 5,598,007 A | 1/1997 | Bunce et al. | 250/566 |
| 5,602,040 A | 2/1997 | May et al. | 436/514 |
| 5,621,204 A | 4/1997 | Yu | 235/462 |
| 5,622,171 A | 4/1997 | Asada et al. | 128/653.1 |
| 5,622,871 A | 4/1997 | May et al. | 436/514 |
| 5,623,939 A | 4/1997 | Garfield | 128/733 |
| 5,627,907 A | 5/1997 | Gur et al. | 382/132 |
| D379,662 S | 6/1997 | Pearson et al. | D24/223 |
| D379,663 S | 6/1997 | Pearson et al. | D24/223 |
| D380,554 S | 7/1997 | Leiva et al. | D24/224 |
| 5,648,274 A | 7/1997 | Chandler | 436/514 |
| 5,654,162 A | 8/1997 | Guire et al. | 435/7.92 |
| 5,654,803 A | 8/1997 | Howard, III et al. | 356/446 |
| 5,656,502 A | 8/1997 | MacKay et al. | 436/180 |
| 5,656,503 A | 8/1997 | May et al. | 436/514 |
| 5,656,506 A | 8/1997 | Kawaguchi et al. | 436/534 |
| 5,658,801 A | 8/1997 | Poissant et al. | 436/518 |
| 5,658,802 A | 8/1997 | Hayes et al. | 436/518 |
| 5,661,563 A | 8/1997 | Howard et al. | 356/446 |
| D383,549 S | 9/1997 | Arnett et al. | D24/223 |
| D383,550 S | 9/1997 | Larson et al. | D24/223 |
| D384,164 S | 9/1997 | Leiva et al. | D24/224 |
| 5,665,310 A | 9/1997 | Augstein | 422/66 |
| 5,668,017 A | 9/1997 | Buchanan et al. | 436/518 |
| 5,681,529 A | 10/1997 | Taguchi et al. | 422/61 |
| 5,686,315 A | 11/1997 | Pronovost et al. | 436/510 |
| 5,687,716 A | 11/1997 | Kaufmann et al. | 128/630 |
| 5,690,103 A | 11/1997 | Groth et al. | 128/632 |
| 5,701,181 A | 12/1997 | Boiarski et al. | 356/446 |
| D390,667 S | 2/1998 | Nazareth | D24/223 |
| 5,715,182 A | 2/1998 | Asai et al. | 364/555 |
| 5,723,868 A | 3/1998 | Hammond, Jr. et al. | 250/553 |
| 5,741,462 A | 4/1998 | Nova et al. | 422/68.1 |
| 5,751,629 A | 5/1998 | Nova et al. | 365/151 |
| 5,817,461 A | 10/1998 | Austin et al. | 435/6 |
| 5,837,546 A | 11/1998 | Allen et al. | 436/169 |
| 5,874,214 A | 2/1999 | Nova et al. | 435/6 |
| 5,878,746 A | 3/1999 | Lemelson et al. | 600/407 |
| 5,925,562 A | 7/1999 | Nova et al. | 435/287.1 |
| 5,961,923 A | 10/1999 | Nova et al. | 422/68.1 |
| 6,017,496 A | 1/2000 | Nova et al. | 422/68.1 |
| 6,025,129 A | 2/2000 | Nova et al. | 435/6 |
| 6,100,026 A | 8/2000 | Nova et al. | 435/6 |
| D432,244 S | 10/2000 | Anderson et al. | D24/223 |
| D434,153 S | 11/2000 | Anderson et al. | D24/216 |

FOREIGN PATENT DOCUMENTS

| | | |
|---|---|---|
| EP | 0500506 | 8/1992 |
| EP | 0610805 | 8/1994 |
| EP | 0616291 | 9/1994 |
| EP | 0644414 | 3/1995 |
| EP | 0359274 | 11/1995 |
| EP | 0528988 | 4/1997 |
| EP | 303110 | 2/1998 |
| JP | 6310157 | 5/1988 |
| JP | 4130247 | 5/1992 |
| JP | 6503645 | 4/1994 |
| JP | 755688 | 3/1995 |
| JP | 862134 | 3/1996 |
| JP | 9119894 | 5/1997 |
| JP | 9178748 | 7/1997 |
| WO | 8808534 | 11/1988 |
| WO | 9210585 | 6/1992 |
| WO | WO92/10585 | * 6/1992 |
| WO | 9425933 | 11/1994 |
| WO | 9427490 | 12/1994 |
| WO | WO96/13707 | * 10/1995 |
| WO | 9612187 | 4/1996 |
| WO | 9705553 | 2/1997 |
| WO | 9709678 | 3/1997 |
| WO | 9717891 | 5/1997 |
| WO | 9729447 | 8/1997 |
| WO | 9737222 | 10/1997 |

OTHER PUBLICATIONS

ANSI MH10.8M–1993, American National Standard *for Materials Handling*– Unti Loads and Transport Packages– Bar Code Symbols. American National Standards Institute, 1994.

"BarCode 1; Code 128 Specification Page", (available on http://www.adams1.com/pub/russadam/128code.html on Apr. 14, 1998).

"Code 39 Symbology", (available on http://www.abetech-.com/abetech/ab . . . /3d40bf6c892a1f6a8625645100586c88 on Apr. 14, 1998).

Lockwood, C. et al., "Fetal Fibronectin in Cervical and Vaginal Secretions as a Predictor of Preterm Delivery", *The New England Journal of Medicine* 325(10):699–74 (1991).

Nageotte et al., "Fetal fibronectin in patients at increased risk for premature birth,", *Am J Obstet Gynecol* 170(1):20–5 (1994).

Press Release: Adeza Biomedical and Biotrin International announce agreement to distribute test for preterm labor, Nov. 18, 1999, http://www/adeza/com/news.htm.

Press Release: Adeza Biomedical and Abbott Laboratories announce agreement to market test for preterm labor, Sep. 2, 1999, http://www/adeza/com/news.htm.

Senyei, A.E. and E.R. Wassman, Fetal Cells in the Maternal Circulation 20(3):583–98 (1993).

Tsay et al., "Optical Biosensor assay (OBA)," *Clinical Chemistry* 37(9):1502–1505 (1991).

"Artificial Intelligence Systems in Routine Clinical Use", (available on http://www.gretmar.com/ailist/list.html on Nov. 21, 1996).

"Neural Informatics Pearls of Wisdom", (available on http://www.smi.stanford.edu/people/...hysiology/Neuro_Pearls.html#ANN–app on Nov. 21, 1996).

Al–Jumah et al., Artificial neural network based multiple fault diagnosis in digital circuits, *Proceedings of the 1998 IEEE International Symposium on Circuits and Systems* 2:304–307 (1998).

Alvager, T., et al., "The Use of Artificial Neural Networks in Biomedical Technologies: An Introduction", *Biomed. Instr. Tech.*, 315–322 (1994).

Baxt, W.G., "A Neural Network Trained to Identify the Presence of Myocaridal Infarction Bases Some Decisions on Clinical Associations that Differ from Accepted Clinical Teaching", *Med. Decis. Making*, 14:217–222 (1994).

Baxt, W.G., "Application of Artificial Neural Networks to Clinical Medicine", *The Lancet*, 346:1135–1138 (1995).

Baxt, W.G., "Analysis of the Clinical Variables Driving Decision in an Artificial Neural Network Trained to Identify the Presence of Myocardial Infarction", *Ann. Emerg. Med.*, 21(12):1439–1444 (1992).

Baxt, W.G., "Use of an Artificial Neural Network for the Diagnosis of Myocardial Infarction", *Ann. Int. Med.*, 115:843–848 (1991).

Baxt, W.G., "Improving the Accuracy of an Artificial Neural Network Using Multiple Differently Trained Networks", *Neur. Comp.*, 4:772–780 (1992).

Baxt, W.G., "Complexity, Chaos and Human Physiology: The Justification for Non–linear Neural Computational Analysis", *Cancer Lett.*, 77:85–93 (1994).

Baxt, W.G., "Use of an Artificial Neural Network for Data Analysis in Clinical Decision–Making: The Diagnosis of Acute Coronary Occlusion", *Neur. Comp.*, 2:480–489 (1990).

Baxt, W.G. and White, H., "Bootstrapping Confidence Intervals for Clinical Input Variable Effects in a Network Trained to Identify the Presence of Acute Myocardial Infarction", *Neur. Comp.*, 7:624–638 (1995).

Beksac, M.S. et al., "An Artificial Intelligent Diagnostic System with Neural Networks to Determine Genetical Disorders and Fetal Health by Using Maternal Serum Markers", *Eur. Jour. Ob. Gyn. Reprod. Bio.*, 59:131–136 (1995).

Benediktsson, J.A., et al., "Parallel Consensual Neural Networks with Optimally Weighted Output", *Proc. World. Cong. Neur. Networks*, 3:129–137 (1994).

BioComp Systems, Inc., "Systems that Learn, Adapt and Evolve", (available on http://www.bio–comp.com/products.htm on Nov. 21, 1996).

Blinowska, A. et al., "Diagnostica –A Bayesian DecisionAid System –Applied to Hypertension Diagnosis", *IEEE Transact. Biomed. Eng.*, 40(3):230–235 (1993).

Brickley, M.R. and Shepherd, J.P., "Performance of a Neural Network Trained to Make Third–molar Treatment–planning Decisions", *Med. Decis. Making*, 16:153–160 (1996).

Brownell, Neural networks for sensor management and diagnostics, *Proceedings of the IEEE Aerospace and Electronics Conference* 3:923–929 (1992).

Creasy, R.K. and Resnik, R., "Maternal–Fetel Medicine: Principles and Practice", Ch.36, Sect.18, p. 657, Harcourt, Brace, Jovanovich, Inc., 1989.

Database Derwent WPI #009580780, citing European patent 557831 A, Instrument for determining optimum delivery time of foetus.

Davis, R. et al., "Production Rules as a Representation for a Knowledge–Based Consultation Program", *Artif. Intel.*, 8:15–45 (1977).

Diller, W., "Horus' Computer–Enhanced Diagnostics", *IN VIVO: Business and Medicine Report*, pp. 3–10 (1997).

Fahlman, S.E., "Faster–Learning Variations on Back–Propagation: An Empirical Study", *Proc. 1988 Connectionist Models Summer School*, Pittsburgh, pp. 38–51 (1988).

Fahlman, S.E. and Lebiere, C., "The Cascade–Correlation Learning Architecture", *Adv. Neur. Informat. Proc. Syst.*, 2:524–532 (1989).

Geoghegan, W.D. and Ackerman, G.A., "Adsorption of Horseradish Peroxidase, Ovomucoid and Anti–Immunoglobulin to Colloidal Gold for the Indirect Detection of Concenevalin A, Wheat Germ Agglutinin and Goat Anti–Human Immunoglobulin G on Cell Surfaces at the Electron Microscopic Level: A New Method, Theory and Application", *Jour. Hist. Cytochem.*, 25(11):1157–1200 (1977).

Kahn, C.E. et al., "Mammonet: Mammography Decision Support System", (available at http://www.mcw.edu/midas/mammo.html on Nov. 21, 1996).

Keller, P.E., "Artificial Neural Networks in Medicine", Handout / Technology brief, Pacific Northwest Laboratory.

Kim, J. et al., "Ensemble Competitve Learning Neural Networks with Reduced Input Dimension", *Int. J. Neur. Syst.*, 6(2):133–142 (1995).

Kol, S. et al. "Interpretation of Nonstress Tests by an Artificial Neural Network", *Am. J. Obstet. Gynecol.*, 172(5):1372–1379 (1995).

LaPuerta, P. et al., "Use of Neural Networks in Predicting the Risk of Coronary Artery Disease", *Comp. Biomed. Res.*, 28:38–52 (1995).

Maclin, P.S. et al., "Using Neural Networks to Diagnose Cancer", *J. Med. Syst.*, 15(1):11–19 (1991).

Marko et al., Automotive diagnostics using trainable classifiers: statistical testing and paradigm selection, *IJCNN International Joint Conference on Neural Networks* 1:33–38 (1990).

Matsuura, H. and Hakomori, S., "The Oncofetal Domain of Fibronectin Defined by Monoclonal Antibody FDC–6; Its Presence in Fibronectins from Fetal and Tumor Tissues and Its Absence in Those from Normal Adult Tissues and Plasma", *Proc. Natl. Acad. Sci. USA*, 82:6517–6521 (1985).

Michel et al., Prognosis with neural networks using statistically based feature sets, *Computer–Based Medical Systems, Proceedings of Fifth Annual IEEE Symposium* pp. 695–702 (1992).

Mobley, B.A. et al., "Artificial Neural Network Predictions of Lengths of Stay on a Post–Coronary Care Unit", *Heart Lung*, 24(3):251–256 (1995).

Modai, I. et al., "Clinical Decisions for Psychiatric Inpatients and their Evaluation by a Trained Neural Network", *Meth. Inform. Med.*, 32(6):396–399 (1993).

Moneta, C. et al., "Automated Diagnosis and Disease Characterization using Neural Network Analysis", IEEE Intl. Conf. Systs., Man, Cybernetics, USA, 1:123–128 (1992).

Nejad, A.F. and Gedeon, T.D., "Significance Measures and Data Dependency in Classification Methods", *IEEE Intl. Conf. Neur. Network Proceedings*, Australia, 4:1816–1822 (1995).

Ota, H. and Maki, M., "Evaluation of Autoantibody and CA125 in the Diagnosis of Endometriosis or Adenomyosis", *Med. Sci. Res.*, 18:309–310 (1990).

Ouyang et al., Using a neural network to diagnose anterior wall myocaridal infarction , *International Conference on Neural Networks* 1:56–61 (1997).

Pattichis, C.S. et al., "Neural Network Models in EMG Diagnosis", *IEEE Trans. Biomed. Engin.*, 42:486–495 (1995).

Penny, W. and Frost, D., "Neural Networks in Clinical Medicine", *Med. Decis. Making*, 16:386–398 (1996).

Pollak, V. and Boulton, A.A., "An Experimental High–Performance Photodensitometer for Quantitative Chromatography", *J. Chromat.*, 115:335–347 (1975).

Press, W.H. et al., eds., "*Nurmerial Recipes in C*", Cambridge University Press, Second Edition, 1992.

Rogers, S.K. et al., "Artificial Neural Networks for Early Detection and Diagnosis of Cancer", 77:79–83 (1994).

Sheppard et al., A neural network for evaluating diagnostic evidence, *Aerospace and Electronics Conference, NAECON, Proceedings of the IEEE 1991 National* 2:717–723 (1991).

Siganos, D., "Neural Networks in Medicine", (available at http://scorch.doc.ic.ac.uk/~nd/surprise_96/journal/vol2/ds12/article2.html on Nov. 21, 1996).

Snow, P.B. et al., "Artificial Neural Networks in the Diagnosis and Prognosis of Prostate Cancer: A Pilot Study", *J. Urol.*, 152:1923–26 (1994).

Solms, F. et al., "A Neural Network Diagnostic Tool for the Chronic Fatigue Syndrome", *International Conference on Neural Networks*, Paper No. 108 (1996).

Stamey, T.A., "ProstAsure™; An Information Resource", (available at http://www.labcorp.com/prost.3.htm on Nov. 21, 1996).

Stephenson, J., "RAMP: A Quantitative Immunoassay Platform Takes Shape", *IVD Tech.*, pp. 51–56 (1996).

Turner, D.D. and Garrett, B.A., "Coronary Artery Disease Diagnosis", Technology handout, (available on http://www.emsl.gov:2080/docs/cie/techbrief/CAD.techbrief.html on Nov. 21, 1996).

Utans, J. et al., "Input Variable Selection for Neural Networks: Application to Predicting the U.S. Business Cycle", *IEEE*, pp. 118–122 (1995).

Utans, J. and Moody, J., "Selecting Neural Network Architectures via the Prediction Risk: Application to Corporate Bond Rating Prediction", *Proceedings of the First International Conference on Artificial Intelligence Applications on Wall Street*, Washington, D.C., IEEE Computer Society Press, pp. 35–41 (1991).

van Dyne et al., "Using machine learning and expert systems to predict preterm delivery in pregnant women", Proceedings of the Tenth Conference on Artificial Intelligence for Applications, San Antonia, TX, Mar. 1–4, 1994, pp. 344–350.

van Dyne et al., "Using inductive machine learning, expert systems and case based reasoning to predict preterm delivery in pregnant women", Database and Expert Systems Applications, 5th Int'l Conf., DEXA 1994 Proceedings, Athens, Greece, Sep. 7–9, 1994, pp. 690–702.

Weinstein, J.N. et al., "Neural Networks in the Biomedical Sciences: A Survey of 386 Publications Since the Beginning of 1991", pp. 121–126.

Widman, L.E., "Expert Systems in Medicine", (available on http://amplatz.uokhsc.edu/acc95–expert–systems.html on Nov. 21, 1996).

Wilding, P. et al., "Application of Backpropagation Neural Networks to Diagnosis of Breast and Ovarian Cancer", *Caner Lett.*, 77:145–153 (1994).

Young, G.P., "Diagnosis of Acute Cardiac Ischemia", (available on http://www.library.ucs...1/Orginals/young.html on Nov. 21, 1996).

* cited by examiner

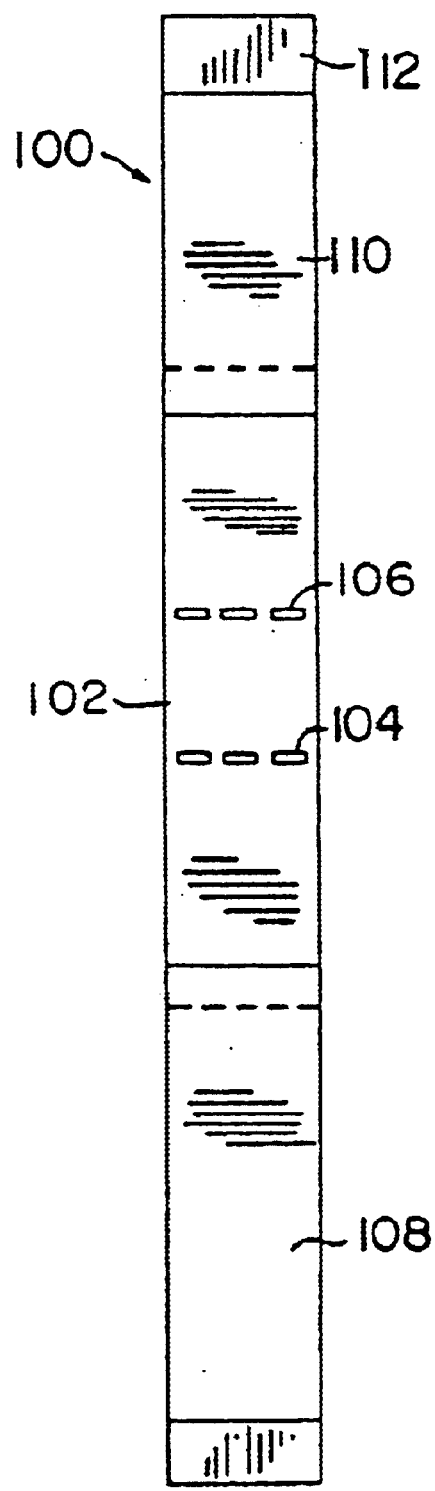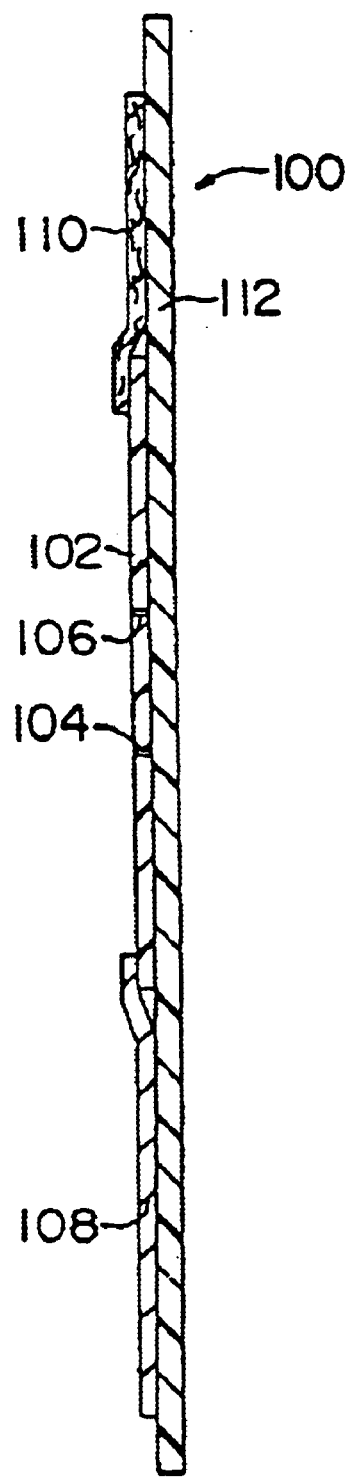
FIG. IA  FIG. IB

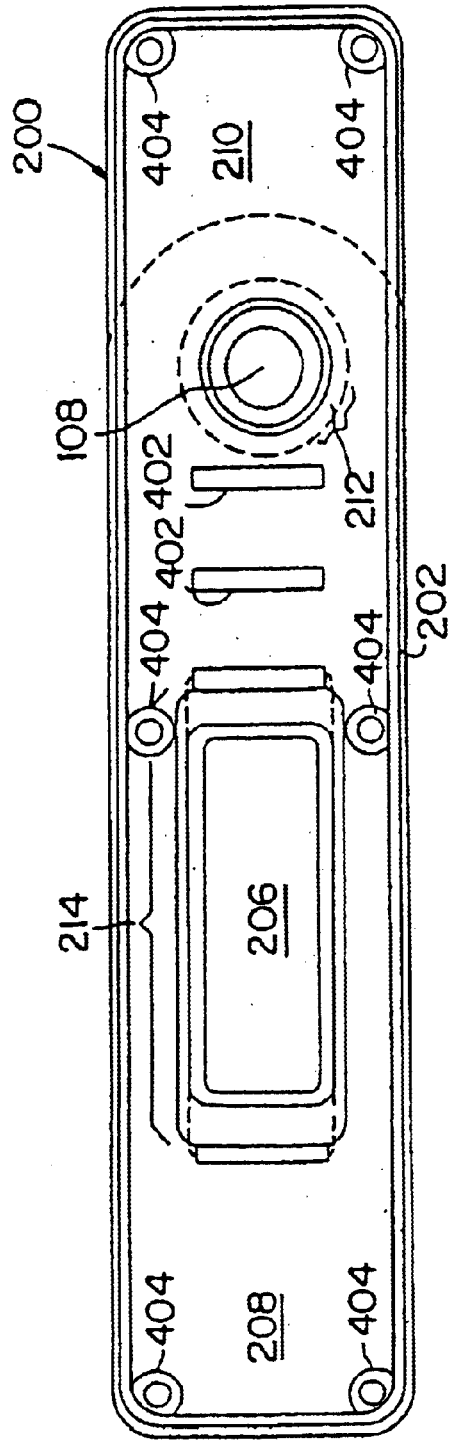
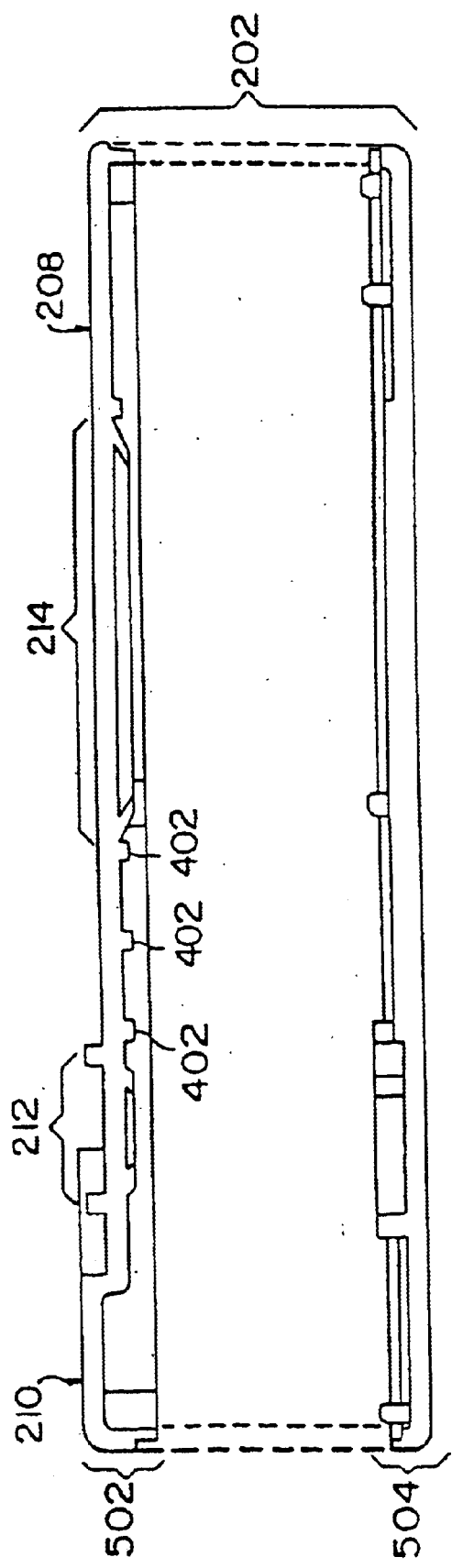
FIG. 4
FIG. 5

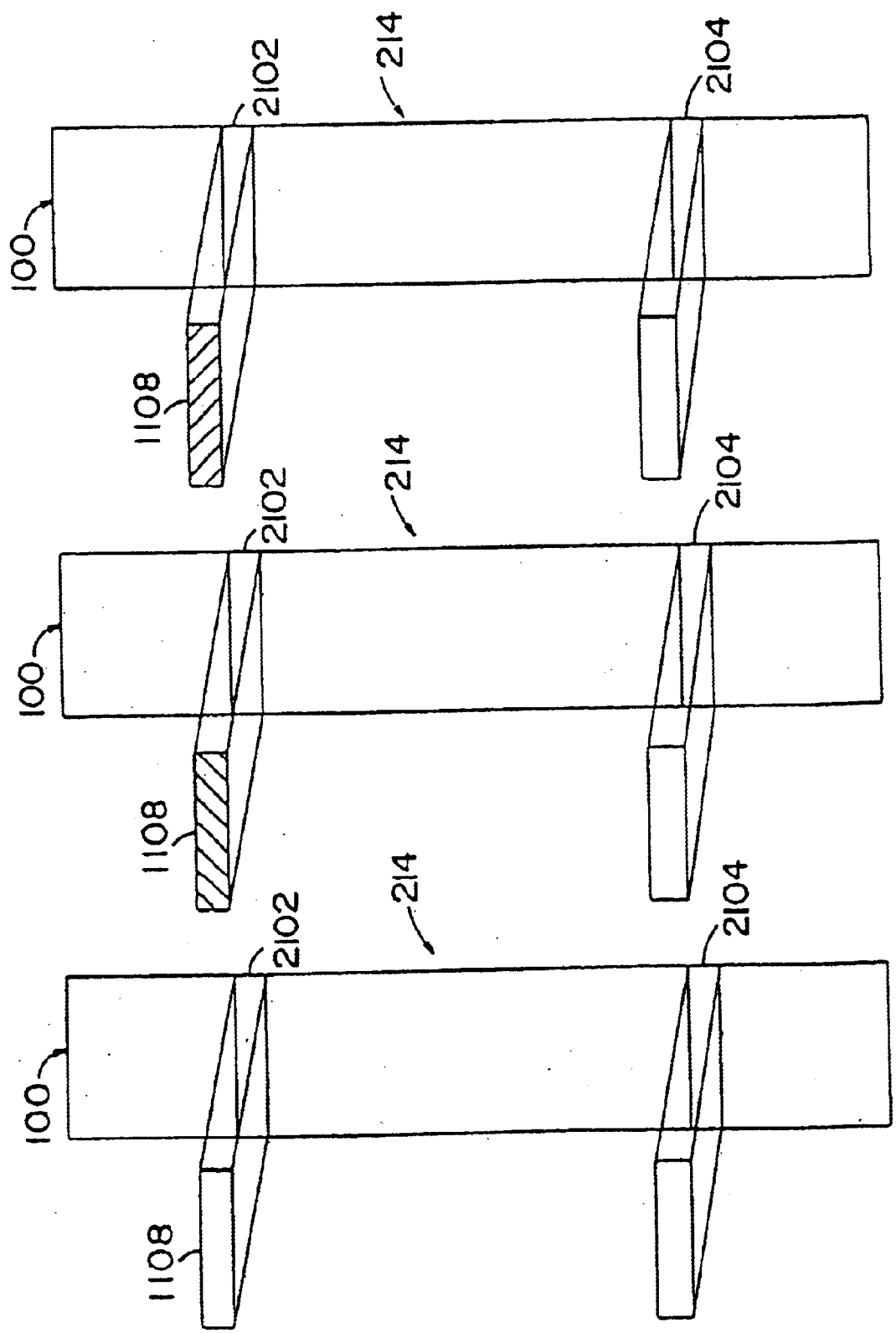

POINT OF CARE DIAGNOSTIC SYSTEMS

RELATED APPLICATIONS

This application is a divisional of U.S. application Ser. No. 09/063,497, filed Apr. 20, 1998 now U.S. Pat. No. 6,394,952, Emory V. Anderson, Edward Nemec, Jerome Lapointe, Duane DeSieno, Ricardo Martinez, Gail Marzolf, Ronald Pong, Lynn Jones, Robert O. Hussa and Andrew Senyei, entitled "POINT OF CARE DIAGNOSTIC SYSTEMS", and a continuation-in-part of U.S. application Ser. No. 09/017,901, filed Feb. 3, 1998 now U.S. Pat. No. 6,267,722 to Emory V. Anderson, Edward Nemec, Jerome Lapointe, Duane DeSieno, Ricardo Martinez, Gail Marzolf, Ronald Pong, Lynn Jones, Robert O. Hussa and Andrew Senyei, entitled "POINT OF CARE DIAGNOSTIC SYSTEMS."

This application is also related to U.S. application Ser. No. 08/599,275 to Jerome Lapointe and Duane DeSieno, filed Feb. 9, 11996, entitled "METHOD FOR DEVELOPING MEDICAL AND BIOCHEMICAL DIAGNOSTIC TESTS USING NEURAL NETWORKS", now abandoned, copending U.S. application Ser. No. 08/798,306 to Jerome Lapointe and Duane DeSieno, filed Feb. 7, 1997, entitled "METHOD FOR SELECTING MEDICAL AND BIOCHEMICAL DIAGNOSTIC TESTS USING NEURAL NETWORK-RELATED APPLICATIONS" and copending U.S. application Ser. No. 08/912,133 to Jerome Lapointe and Duane, DeSieno, filed Aug. 14, 1997, entitled "METHOD FOR SELECTING MEDICAL AND BIOCHEMICAL DIAGNOSTIC TESTS USING NEURAL NETWORK-RELATED APPLICATIONS".

This application is also related to U.S. Pat. Nos. 5,096,890, 5,185,270, 5,223,440, 5,236,846, 5,281,522, 5,468,619 and 5,516,702.

The subject matter of each of the above noted patents and of each of the above-noted patent applications is incorporated herein by reference in its entirety. The subject matter of published International PCT application No. WO 97/29447, which corresponds to U.S. application Ser. No. 08/912,133 is also herein incorporated in its entirety by reference thereto. Design patent application Nos. 29/086,781 and 29/086,799, each filed Apr. 20, 1998, now U.S. Patent Nos. D43453 respectively, are also incorporated by reference herein.

FIELD OF THE INVENTION

The present invention relates to systems and methods that aid in providing a medical diagnosis or risk assessment for a patient using biochemical and historic patient data, including data from point of care diagnostic tests or assays, and processing the information to give an indication of a medical condition or risk.

BACKGROUND OF THE INVENTION

Evaluation of Immunoassay Data

In diagnostic immunochromatographic assays, where results are determined by a color change or the production of color, results are generally detected visually by human eye. As a result of the human perception and judgment involved, there is significant variance among those interpreting such test results as to whether a color change or other measurable signal has occurred--; and the degree of such occurrence. Furthermore, there is a great deal of subjectivity involved in interpreting whether immunoassay results are positive or negative. This is particularly pronounced where the result is close to a threshold value. The variance is further enhanced when attempts are made to quantitate such assay test results. Accurate results may be critical for certain diagnostic assays.

It is desirable to develop techniques that are objective in nature; and that reduce the error associated with interpreting immunochromatographic and other assay test results. Therefore, it is an object herein to provide systems, methods, devices and instruments for objectively assessing data from biochemical and other tests and to use such data for diagnosis and risk assessment. It is also an object herein to incorporate decision-support methodologies into such systems and thereby enhance the diagnostic and risk assessment capabilities thereof.

It is also an object herein to provide systems and methods for use in detecting and measuring fetal fibronectin (fFN) levels in a patient sample and using such information to diagnose and assess risks of preterm labor, fetal membrane rupture and other related disorders and conditions.

SUMMARY OF THE INVENTION

Systems and methods for medical diagnosis or risk assessment for a patient are provided. These systems and methods are designed to be employed at the point of care, such as in emergency rooms, operating rooms, hospital laboratories and other clinical laboratories, doctor's offices, in the field, or in any situation in which a rapid and accurate result is desired. The systems and methods process patient data, particularly data from point of care diagnostic tests or assays, including immunoassays, chemical assays, nucleic acid assays, calorimetric assays, fluorometric assays, chemiluminescent and bioluminescent assays, electrocardiograms, X-rays and other such tests, and provide an indication of a medical condition or risk or absence thereof.

The systems include an instrument for reading or evaluating the test data and software for converting the data into diagnostic or risk assessment information. In certain embodiments, the systems include a test device, such as a test strip, optionally encased in a housing, for analyzing patient samples and obtaining patient data. In particular embodiments, the device includes a symbology, such as a bar code, which is used to associate identifying information, such as intensity value, standard curves, patient information, reagent information and other such information, with the test device. The reader in the system is optionally adapted to read the symbology.

Further, the systems optionally include a decision-support system or systems, such as a neural network, for evaluating the digitized data, and also for subsequent assessment of the data, such as by integration with other patient information, including documents and information in medical records. All software and instrument components are preferably included in a single package. Alternatively, the software can be contained in a remote computer so that the test data obtained at a point of care can be sent electronically to a processing center for evaluation. Thus, the systems operate on site at the point of care, such as in a doctor's office, or remote therefrom.

The patient information includes data from physical and biochemical tests, such as immunoassays, and from other procedures. The test is performed on a patient at the point of care and generates data that can be digitized, such as by an electronic reflectance or transmission reader, which generates a data signal. The signal is processed using software employing data reduction and curve fitting algorithms, or a decision support system, such as a trained neural network, or combinations thereof, for converting the signal into data, which is used to aid in diagnosis of a medical condition or determination of a risk of disease. This result may be further entered into a second decision support system, such as a neural net, for refinement or enhancement of the assessment.

In a particular embodiment, systems and methods for detecting and measuring levels of a target analyte in a patient sample, analyzing the resulting data, and providing a diagnosis or risk assessment are provided. The systems and methods include an assay device in combination with a reader, particularly a computer-assisted reader, preferably a reflectance reader, and data processing software employing data reduction and curve fitting algorithms, optionally in combination with a trained neural network for accurately determining the presence or concentration of analyte in a biological sample. The methods include the steps of performing an assay on a patient sample, reading the data using a reflectance reader and processing the reflectance data using data processing software employing data reduction algorithms. In a particular embodiment, the assay is an immunoassay. Preferred software includes curve fitting algorithms, optionally in combination with a trained neural network, to determine the presence or amount of analyte in a given sample. The data obtained from the reader then can be further processed by the medical diagnosis system to provide a risk assessment or diagnosis of a medical condition as output. In alternative embodiments, the output can be used as input into a subsequent decision support system, such as a neural network, that is trained to evaluate such data.

In a preferred embodiment, the assay device is a lateral flow test strip, preferably, though not necessarily, encased in a housing, designed to be read by the reader, and the assay is a sandwich immunoassay. For example, in one embodiment thereof, a patient sample is contacted with an antibody for a selected target analyte indicative of a disease, disorder or risk thereof. The antibody is preferably labeled by conjugation to a physically detectable label and; and upon contacting with the sample containing the target analyte forms a complex. The antibody-analyte; complex is then contacted with a second antibody for the antigen, which is immobilized on a solid support. The second antibody captures the antibody-analyte complex to form an antibody-analyte-antibody sandwich complex, and the resulting complex, which is immobilized on the solid support, is detectable by virtue of the label. The test strip is then inserted into a reader, where the signal from the label in the complex is measured. Alternatively, the test strip could be inserted into the reader prior to addition of the sample. Additionally, the housing may include a symbology, such as a bar code, which is also read by the reader and contains data related to the assay device and/or test run. The signal obtained is processed using data processing software employing data reduction and curve fitting algorithms, optionally in combination with a trained neural network, to give either a positive or negative result, or a quantitative determination of the concentration of analyte in the sample, which is correlated with a result indicative of a risk or presence of a disease or disorder. This result can optionally be input into a decision support system; and processed to provide an enhanced assessment of the risk of a medical condition as output. The entire procedure may be automated and/or computer-controlled.

In certain embodiments, the reflectance reader is adapted to read a symbology on the test device. The symbology is preferably a bar code, which can be read in the same manner that the test strip in the device can be read. In these embodiments, the reader head scans across a bar code in a stepwise fashion. The data collected from the bar code is transformed into integrated peak information and analyzed as alphanumeric characters, which are related to information related to the particular device and/or test run or other information, including patient information. Any bar code from among the many known in the in industry. In preferred embodiments, Code 39 (a trademark of Interface Mechanism, Inc., Lynnwood, Wash.; see, e, U.S. Pat. No. 4,379,224, U.S. Pat. No. 4,438,327, U.S. Pat. No. 4,511,259 or Code 128 bar codes (see, e.g., U.S. Pat. No. 5,227,893) are used.

In a particular embodiment, the analyte to be detected is fetal fibronectin (fFN) and the result obtained is a positive or negative indication of pregnancy or the risk of certain pregnancy-related conditions or fertility and infertility-related conditions, including ectopic pregnancy, preterm labor, pre-eclampsia, imminent delivery, term induction and fetal membrane rupture. Thus, provided herein is a rapid fFN test using a lateral flow test device.

At the very least, this test provides the same clinically relevant information as a fFN ELISA (an enzyme linked immunosorbent sandwich assay (ELISA)) test heretofore available in significantly less time and at the point of care. The fFN immunoassay provided herein allows the user to test a cervicovaginal swab sample in about 20 minutes. When practiced as described herein, additional information, such as a more accurate risk assessment or diagnosis, can be obtained.

The system herein provides a means to detect and to quantitate concentrations of fFN throughout pregnancy and to assess the risk and detect conditions associated therewith. Because of the sensitivity of the combination of the reader and devices provided herein, fFN may be monitored throughout pregnancy, including times when it is not detected by less sensitive systems.

The reflectance reader and test strip device are also provided herein. Also provided herein are the neural nets for assessing the data.

A method for classifying an image is also provided. The method includes the steps of reducing the image to a set of derived parameters from which the image can be reconstructed within a predetermined degree of tolerance; inputting the derived parameters into a classification neural network; and determining the classification of the image based on the output of the classification neural network. The method of reducing the image to a set of derived parameters is achieved by defining a mathematical function that contains a plurality of parameters representative of the image; and optimizing the parameters of the function using a methodology that minimizes the error between the image and a reconstruction of the image using the function.

In an alternative embodiment, the method of reducing the image to a set of derived parameters is achieved by inputting the image into a trained neural network, where the inputs to the network represent the with image the hidden layer of the network is such that the number of hidden elements is smaller than the number of inputs to the network, and the outputs of the network represent reconstruction of the image; and setting the derived parameters to the output values of the trained neural network.

In another alternative embodiment, the method of reducing the image to a set of derived parameters is achieved by defining a neural network in which the inputs to the network are the coordinates of a point in the image, the hidden layer contains a plurality of elements, and the output of the network represents the reconstruction of the associated point in the image; training the neural network so that the error between the network output and the image are minimized for all points in the with image, and setting the derived parameters to the weights of the hidden layer of the trained neural network.

The neural networks and computer systems used in the methods are also provided.

BRIEF DESCRIPTION OF THE DRAWINGS

FIG. 1A is a top view of an assay test strip, such as an immunoassay test strip;

FIG. 1B is a side view of the assay test strip of FIG. 1A;

FIG. 4 is a top view of an exemplary housing assembly for the assay test strip of FIGS. 1A and 1B;

FIG. 5 is a side assembly view of the housing assembly of FIG. 4;

FIG. 21 is a schematic diagram illustrating a process by which an assay test strip is analyzed so as to determine an amount of background light at a control region of the assay test strip;

FIG. 22 is a schematic diagram illustrating a process by which an assay test strip is analyzed so as to determine an amount of reflection resulting from a first illumination of a control portion of the assay test strip; and FIG. 23 is a schematic view diagram illustrating a process by which an assay test strip is analyzed so as to determine an amount of reflection resulting from a second illumination of a control portion of the assay test strip;

DETAILED DESCRIPTION OF PREFERRED EMBODIMENTS

Definitions

Figure 2A:
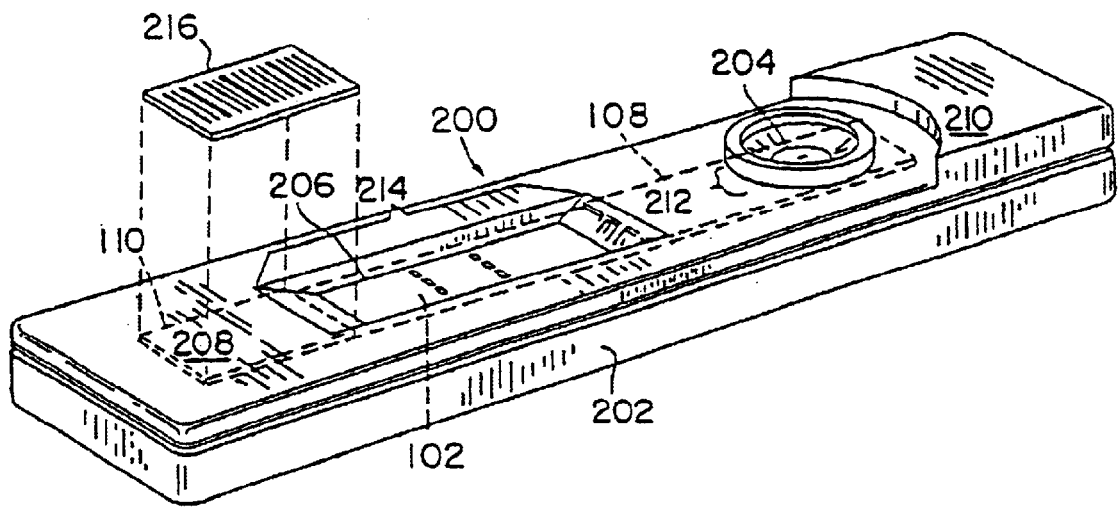
FIG. 2A is a perspective view of an assay device, including the assay test strip of FIG. 1A and FIG. 1B and housing assembly and showing a bar code, which can optionally be affixed to the housing.

Unless defined otherwise, all technical and scientific terms used herein have the same meaning as is commonly understood by one of skill in the art to which this invention belongs. All patents and publications referred to herein are, unless noted otherwise, incorporated by reference in their entirety. In the event a definition in this section is not consistent with definitions elsewhere, the definition set forth in this section will control.

As used herein, point of care testing refers to real time diagnostic testing that can be done in a rapid time frame so that the resulting test is performed faster than comparable tests that do not employ this system. For example, the exemplified fFN immunoassay, is performed in less time than the fFN ELISA assay (i.e., less than about 3 to 4 hours, preferably less than 1 hour, more preferably less than half an hour). In addition, with the method and devices provided herein, it can be performed rapidly and on site, such as in a doctor's office, at a bedside, in a stat laboratory, emergency room or other such locales, particularly where rapid and accurate results are required. The patient can be present, but such presence is not required. Point of care includes, but is not limited to: emergency rooms, operating rooms, hospital laboratories and other clinical laboratories, doctor's offices, in the field, or in any situation in which a rapid and accurate result is desired.

As used herein, an anti-fFN antibody is an antibody that binds selectively with fFN. Such antibodies are known to those of skill in the art and also may be readily isolated.

As used herein, a test strip refers to any means on which patient test data or other data is generated, recorded or displayed in a manner that forms an image or from which an image can be generated. Such strips, include, but are not limited to, immunochromatographic test strips, such as lateral flow devices, X-ray films, such as X-rays and films produced from sequencing gels, EKG printouts, MRI results and other such means that generate or from which an image as defined herein can be generated. The strip is preferably adapted for scanning or reading by a reader, preferably the reader provided herein. Although referred to as a "strip", it can be of any shape or geometry, including rectangular, three dimensional, circular, and so forth.

As used herein, a sigmoidal pattern (also referred to herein as sigmoidal-like; see, e.g., FIG. 19) with reference to the fiberoptics refers to the S-shaped or snake-like pattern of illumination selected for maximizing illumination across the lines on the test strip. The pattern is not strictly a sigmoidal shape, but refers to a pattern such as that depicted in FIG. 19, which pattern provides a means for adding more area to any reading. Any other pattern that achieved this result is encompassed within this expression.

As used herein, quantitative results are results that are absolute or relative values; qualitative results are typically negative or positive type results.

As used herein, fetal restricted antigens refers to antigen that are present in pregnant women uniquely, or in substantially elevated amounts compared to non-pregnant women in maternal serum, plasma, urine, saliva, sweat, tears and other bodily fluids.

As used herein, fetal fibronectin is a fetal restricted antigen found in placenta, amniotic fluid and fetal connective tissue. It differs structurally from adult fibronectins. Fetal fibronectin is not present in significant quantities in maternal plasma or serum. Fetal fibronectin may be captured with a general binding antibody, such as an anti-fibronectin antibody, or an anti-fetal restricted antigen antibody, such as anti-fetal fibronectin antibody.

As used herein, an immunoassay is defined as any method using a preferential binding of an antigen with a second material, a binding partner, usually an antibody or another substance having an antigen binding site, which binds preferentially with an epitope of the fetal restricted antigen. Preferential binding, as used herein, refers to binding between binding partners that is selective and generally specific, and demonstrates less than 10%, preferably less than 5%, cross-reactive nonspecific binding. The immunoassay methods provided herein include any known to those of skill in the art, including, but not limited to, sandwich, competition, agglutination or precipitation, for example.

As used herein, a solid support refers to the material to which the antibody is linked. A variety of materials can be used as the solid support. The support materials include any material that can act as a support for attachment of the molecules of interest. Such materials are known to those of skill in this art. These materials include, but are not limited to, organic or inorganic polymers, natural and synthetic polymers, including, but not limited to, agarose, cellulose, nitrocellulose, cellulose acetate, other cellulose derivatives, dextran, dextran-derivatives and dextran co-polymers, other polysaccharides, glass, silica gels, gelatin, polyvinyl pyrrolidone, rayon, nylon, polyethylene, polypropylene, polybutlyene, polycarbonate, polyesters, polyamides, vinyl polymers, polyvinylalcohols, polystyrene and polystyrene copolymers, polystyrene cross-linked with divinylbenzene or the like, acrylic resins, acrylates and acrylic acids, acrylamides, polyacrylamides, polyacrylamide blends, copolymers of vinyl and acrylamide, methacrylates, methacrylate derivatives and co-polymers, other polymers and co-polymers with various functional groups, latex, butyl rubber and other synthetic rubbers, silicon, glass, paper, natural sponges, insoluble protein, surfactants, red blood cells, metals, metalloids, magnetic materials, or other commercially available media.

As used herein, a reader refers to an instrument for detecting and/or quantitating data, such as on test strips. The data may be visible to the naked eye; does not need to be visible.

As used herein, a reflectance reader refers to an instrument adapted to read a test strip using reflected light, including fluorescence, or electromagnetic radiation of any wavelength. Reflectance can be detected using a photodetector or other detector, such as charge coupled diodes (CCD). A preferred reflectance reader, which is provided and described herein, includes a cassette slot adapted to receive a test-strip, light-emitting diodes, optical fibers, a sensing head, including means for positioning the sensing head along the test strip, a control circuit to read the photodetector output and control the on and off operation of the light-emitting diodes, a memory circuit for storing raw and/or processed data, and a photodetector, such as a silicon photodiode detector.

As used herein, a sensing head refers to the assembly which is adapted to read a test strip using reflected light or other electromagnetic radiation. Thus, the sensing head in the reader provided herein refers to the part of the sensing head assembly that randomizes the optical bundles and arranges the fibers in the plane normal to the test strip.

As used herein, color refers to the relative energy distribution of electromagnetic radiation within the visible spectrum. Color can be assessed visually or by using equipment, such as a photosensitive detector.

As used herein, a color change refers to a change in intensity or hue of color or may be the appearance of color where no color existed or the disappearance of color.

As used herein, a decision-support system, also referred to as a "data mining system" or a "knowledge discovery in data system", is any system, typically a computer-based system, that can be trained on data to classify the input data and then subsequently used with new input data to make decisions based on the training data. These systems include, but are not limited, expert systems, fuzzy logic, non-linear regression analysis, multivariate analysis, decision tree classifiers, Bayesian belief networks and, as exemplified herein, neural networks.

As used herein, an adaptive machine learning process refers to any system whereby data are used to generate a predictive solution. Such processes include those effected by expert systems, neural networks, and fuzzy logic.

As used herein, an expert system is a computer-based problem solving and decision-support system based on knowledge of its task and logical rules or procedures for using the knowledge. The knowledge and the logic are entered into the computer from the experience of human specialists in the area of expertise.

As used herein, a neural network, or neural net, is a parallel computational model comprised of densely interconnected adaptive processing elements. In the neural network, the processing elements are configured into an input layer, an output layer and at least one hidden layer. Suitable neural networks are known to those of skill in this art (see, e.g., U.S. Pat. Nos. 5,251,626; 5,473,537; and 5,331,550, Baxt (1991) "Use of an Artificial Neural Network for the Diagnosis of Myocardial Infarction," *Annals of Internal Medicine* 115:843; Baxt (1992) "Improving the Accuracy of an Artificial Neural Network Using Multiple Differently Trained Networks," *Neural Computation* 4:772; Baxt (1992) "Analysis of the clinical variables that drive decision in an artificial neural network trained to identify the presence of myocardial infarction," *Annals of Emergency Medicine* 21:1439; and Baxt (1994) "Complexity, chaos and human physiology: the justification for non-linear neural computational analysis," *Cancer Letters* 77:85).

As used herein, a processing element, which may also be known as a perceptron or an artificial neuron, is a computational unit which maps input data from a plurality of inputs into a single binary output in accordance with a transfer function. Each processing element has an input weight corresponding to each input which is multiplied with the signal received at that input to produce a weighted input value. The processing element sums the weighted inputs values of each of the inputs to generate a weighted sum which is then compared to the threshold defined by the transfer function.

As used herein, a transfer function, also known as a threshold function or an activation function, is a mathematical function which creates a curve defining two distinct categories. Transfer functions may be linear, but, as used in neural networks, are more typically non-linear, including quadratic, polynomial, or sigmoid functions.

As used herein, an image is a multi-dimensional array of data points, where each data point is represented by a number, or a set of numbers, and where there is a relationship between adjacent points in each of the dimensions. The index values in each dimension typically represent a linear relationship, like position or time, but are not limited to these types of relationships. A single digitized scan line from a TV frame would be considered a two dimensional image. In the case of the preferred embodiment, an image refers to a one-dimensional set of pixels, which encode the intensity of the color on the test strip.

As used herein, classifying an image refers to associating an object or state with the image. Images of fruit might be classified as to the type of fruit shown in the image. In the case of the preferred embodiment, classifying the test strip image refers to associating the positive or negative state with the image.

As used herein, reconstructing an image refers to producing an image from a mathematical function. When an image is represented by a mathematical function, there may be errors in the representation due to any number of factors.

As used herein, backpropagation, also known as backprop, is a training method for neural networks for correcting errors between the target output and the actual output. The error signal is fed back through the processing layer of the neural network, causing changes in the weights of the processing elements to bring the actual output closer to the target output.

As used herein, Quickprop is a backpropogation method that was proposed, developed and reported by Fahlman ("Fast Learning Variations on Back-Propagation: An Empirical Study", *Proceedings on the 1988 Connectionist Models Summer School*, Pittsburgh, 1988, D. Touretzky, et al., eds., pp.38–51, Morgan Kaufmann, San Mateo, Calif.; and, with Lebriere, "The Cascade-Correlation Learning Architecture", *Advances in Neural Information Processing Systems* 2, (Denver, 1989), D. Touretzky, ed., pp. 524–32. Morgan Kaufmann, San Mateo, Calif.).

As used herein, diagnosis refers to a predictive process in which the presence, absence, severity or course of treatment of a disease, disorder or other medical condition is assessed. For purposes herein, diagnosis will also include predictive processes for determining the outcome resulting from a treatment.

As used herein, risk refers to a predictive process in which the probability of a particular outcome is assessed.

As used herein, a patient or subject includes any mammals for whom diagnosis is contemplated. Humans are the preferred subjects.

As used herein, biochemical test data refers to data from any analytical methods, which include, but are not limited to: immunoassays, bioassays, including nucleic acid and protein based assays, chromatography, data from monitors, and imagers; measurements and also includes data related to vital signs and body function, such as pulse rate, temperature, blood pressure, data generated by, for example, EKG, ECG and EEG, biorhythm monitors and other such information. The analysis can assess for example, chemical analytes, serum markers, antibodies, protein, nucleic acids and other such material obtained from the patient through a sample. Immunoassays are exemplified herein, but such exemplification is not intended to limit the intended scope of the disclosure, which is applicable to any test strip and test data read by an instrument, particularly a reflectance reader.

As used herein, patient historical data refers to data obtained from a patient, such as by questionnaire format, but typically does not include biochemical test data as used herein, except to the extent such data is historical A; desired solution is one that generates a number or result whereby a diagnosis of a disorder can be generated.

As used herein, a run is defined as a group of tests that include a at least one of a positive reference, positive control, negative control and any number of clinical samples within a 24 hr. period.

As used herein, symbology refers to a code, such as a bar code, that is engraved or imprinted on the test device. The symbology is any code known or designed by the user. The symbols are associated with information stored in a remote computer or memory or other such device or means. For example, each test device can be uniquely identified with an encoded symbology. It is contemplated herein that identifying and other information can be encoded in the bar code, which can be read by the reader when the test strip is read. Alternatively, the bar code or other symbology may be read by any of reading device known to those of skill in the art.

As used herein, a bar code is a symbology, typically a field of alternating dark bars and reflective spaces of varying widths, that is affixed onto or associated with an item and provides identifying information about the item. Bar codes can be placed on a reflective background, and the contrast between the dark bars and reflective spaces, or the reflectivity ratio, allows an optical sensor in a reader to discern the transitions between the bars and spaces in the symbol. Bar codes are electro-optically scanned, typically using a laser or LED, and generate a signal that is transmitted to an associated computer whose memory has digitally stored therein identifying information associated with the item. The item is thereby automatically identified by its bar code and can be tracked, or additional information can be added to the stored information associated with the encoded item.

Several bar code formats are available and are used for differ purposes. A number of different bar code symbologies exist. These symbologies include UPC/EAN codes, Code 39, Code 128, Codeabar, Interleaved 2 of 5 and many others; two-dimensional codes, such as PDF 417, Code 49, Code 16K; matrix codes (Data Code, Code 1, Vericod); graphic codes; and any others known to those of skill in the art. Preferred herein are one-dimensional codes, such as the well known Code 39 and Code 128, although two-dimensional codes (see, e.g., U.S. Pat. Nos. 5,243,655 and 5,304,786, are also suitable for use herein.

The 39 bar code was developed in 1974 to provide a fully alphanumeric bar code for data entry systems. This bar code is especially effective in applications that use alphanumeric data for item identification. The structure of 39 permits it to be printed by a wide variety of techniques, including offset, letterpress, fully-formed impact printers, dot matrix printers, and on-impact printing devices.

Current application areas include inventory control, manufacturing work-in-process, tracking, wholesale distribution, hospitals, government agencies and retail point of sale. Code 39 is the most widely used alphanumeric bar code. It has been accepted as a standard code by many companies and industries. Specification ANSI Draft MH10.X-1981, entitled, "Specifications for Bar Code Symbols on Transport Packages & Unit Loads," describes three different bar code symbologies. Code 39 is called 3-of-9 code in the ANSI specification. Moreover, the Depae MIL-STD-1189, dated Jan. 4, 1982, defines 39 (called 3 of 9 code) as the standard symbology for marking unit packs, outer containers, and selected documents.

Code 39 includes 9 bits, at least three of which are always 1. Code 39 can be used to encode a set of 43 characters, including upper case alphabetic and numeric (0–9) characters, as well as seven special characters (-, ., , *, $, /, + and %). The beginning and end characters are always an asterisk (*). The code uses narrow and wide bars along with narrow and wide spaces, and the encoding for a single character is made up of a pattern of bars and spaces. The code structure is three wide elements out of a total of nine elements, where an element is the area occupied by a bar or space). The nine elements include five bars and four spaces.

In Code 128, every character is constructed of eleven bars and spaces, and all 128 ASCII characters, i.e., numeric characters, upper and lower case characters, punctuation and control codes are encoded. There are three different character sets to select from: one set encodes all upper case characters and all ASCII control characters; another encodes all upper and lower case characters; and the third encodes all numeric characters. Through the use of special characters, it is possible to switch between character sets within a single code symbol. Code 128 uses four different bar and space widths. Each data character encoded in a Code 128 symbol is made up of 11 black or white modules. Three bars and three spaces are formed out of the 11 modules. There are 106 different three bar/three space combinations. Bars and spaces can vary between one and four modules wide. The stop character is made up of 13 modules. The symbol includes a quiet zone (10×-dimensions), a start character, the encoded data, a check character, the stop character and a trailing quiet zone (10×-dimensions) (see, e., U.S. Pat. No. 5,262,625).

Systems for generating and reading bar codes are readily available and are well known in the art.

Point of Care Diagnostic and Risk Assessment Systems

Provided herein are systems for use at the point of care for diagnosing and assessing certain medical risks. The systems are designed for use on site at the point of care, where patients are examined and tested, and for operation remote from the site.

The systems are designed to accept input in the form of patient data, including, but not limited to biochemical test data, physical test data, historical data and other such data, and to process and output information, preferably data relating to a medical diagnosis or a disease risk indicator. The patient data may be contained within the system, such as medical records or history, or may be input as a signal or image from a medical test or procedure, for example, immunoassay test data, blood pressure reading, ultrasound, X-ray or MRI, or introduced in any other form. Specific test data can be digitized, processed and input into the medical diagnosis expert system, where it may be integrated with other patient information. The output from the system is a disease risk index or medical diagnosis.

In a preferred embodiment, the system includes a reader, such as a reflectance or transmission reader, preferably a reflectance reader, for reading patient data, a test device designed to be read in the reader, and software for analysis of the data. In an exemplified embodiment of the system, the reader is the reflectance reader provided herein. A test strip device in a plastic housing designed for use with the reader, optionally including a symbology, such as an alphanumeric character bar code or other machine-readable code, and software designed for analysis of the data generated from the test strip are also provided.

Assays

Any assay is intended for use in the systems and methods herein. Such assays include, but are not limited to: nucleic acid detection, including using amplification and non-amplification protocols and any assay that relies on colorimetric or spectrometric detection, including fluorometric, luminescent detection, such as creatine, hemoglobin, lipids, ionic assays, and blood chemistry. Any test that produces a signal, or from which a signal can be generated, that can be detected by a detector, such as a photodetector or a gamma counter, is intended for use as part of the systems provided herein. Any wavelength is intended to be included.

Immunoassays, including competitive and non-competitive immunoassays, are among those preferred for determination of the presence or amount of analyte in a patient sample, and are exemplified herein. It is understood that immunoassays are provided for exemplification; and that the methods and systems provided herein have broad applicability to patient test data and other test data.

A number of different types of immunoassays are well known using a variety of protocols and labels. Immunoassays may be homogeneous, i.e. performed in a single phase, or heterogeneous, where antigen or antibody is linked to an insoluble solid support upon which the assay is performed. Sandwich or competitive assays may be performed. The reaction steps may be performed simultaneously or sequentially. Threshold assays may be performed, where a predetermined amount of analyte is removed from the sample using a capture reagent before the assay is performed, and only analyte levels of above the specified concentration are detected. Assay formats include, but are not limited to, for example, assays performed in test tubes, wells or on immunochromatographic test strips, as well as dipstick, lateral flow or migratory format immunoassays.

Any known immunoassay procedure, particularly those that can be adapted for use in combination with lateral flow devices as described herein, can be used in the systems and methods provided herein.

Test Device

Any device which is compatible for use with a reader, preferably: a reflectance reader, for determining the assay result is contemplated for use herein. Any such test strips that can be adapted for use in combination with a reader are contemplated for use in the systems provided herein. Such test strip devices as are known to those of skill in the art (see, e.g., U.S. Pat. Nos. 5,658,801, 5,656,502, 5,591,645, 5,500, 375, 5,252,459, 5,132,097 and many other examples) may be used in systems as described herein, particularly in combination with the reader provided herein.

Typically these test devices are intended for use with biological samples, such as saliva, blood, serum, cerebral spinal fluid and cervicovaginal samples, for example. Other biological samples, such as food samples, which are tested for contamination, such as by bacteria or insects, are also contemplated. Target analytes include, but are not limited to: nucleic acids, proteins, peptides, such as human immunodeficiency virus (HIV) antigens, antigens indicative of bacteria such as *Salmonella* and *E. coli*, yeast or parasitic infections, apolipoprotein(a) and lipoprotein(a), environmental antigens, human chorionic gonadotropin (hCG), E-3-G, interleukins and other cytokines and immunomodulatory proteins, such as IL-6 and interferon, small nuclear ribonuclear particles (snRNP) antigens, fFN and other indicators, such as IGF binding protein-1, of pregnancy related disorders.

Immunoassay Test Strip

A preferred embodiment is an immunoassay test strip that includes a membrane system that defines a liquid flow pathway. An exemplary immunoassay test strip provided herein is shown in FIGS. 1A and 1B. The test strip is described in detail in EXAMPLE 1. This test strip is provided for purposes of exemplification of the methods and systems provided herein and is not intended to limit the application to immunoassay test strip devices.

For performing immunoassays, lateral flow test immunoassay devices are among those preferred herein. In such devices, a membrane system forms a single fluid flow pathway along the test strip. The membrane system includes components that act as a solid support for immunoreactions. For example, porous or bibulous or absorbent materials may be placed on a strip such that they partially overlap, or a single material can be used, in order to conduct liquid along the strip. The membrane materials may be supported on a backing, such as a plastic backing. In a preferred embodiment, the test strip includes a glass fiber pad, a nitrocellulose strip and an absorbent cellulose paper strip supported on a plastic backing.

Antibodies that react with the target analyte and/or a detectable label system are immobilized on the solid support. The antibodies may be bound to the test strip by adsorption, ionic binding, van der Waals adsorption, electrostatic binding, or by covalent binding, by using a coupling agent, such as glutaraldehyde. For example, the antibodies may be applied to the conjugate pad and nitrocellulose strip using standard dispensing methods, such as a syringe pump, air brush, ceramic piston pump or drop-on-demand dispenser. In a preferred embodiment, a volumetric ceramic piston pump dispenser is used to stripe antibodies that bind the analyte of interest, including a labeled antibody conjugate, onto a glass fiber conjugate pad and a nitrocellulose strip.

The test strip may or may not be otherwise treated, for example, with sugar to facilitate mobility along the test strip or with water-soluble non-immune animal proteins, such as albumins, including bovine (BSA), other animal proteins, water-soluble polyamino acids, or casein to block non-specific binding sites.

Test Strip Housing

The test strip optionally may be contained within a housing for insertion into the reflectance reader. The housing may be made of plastic or other inert material that does not interfere with the assay procedure. An exemplary assay device, including a test strip and housing assembly is shown in FIGS. 2A–5.

In a preferred embodiment, the test strip housing includes a symbology, such as a bar code that can be associated with data related to the assay device, patient data and/or test run. For example, information associated with the device, such as lot number, expiration date, analyte and intensity value, or information related to the test run, such as date, reflectance value or other such information, can be encoded and associated, such as in a database with a bar code imprinted on the device. Any bar code system that provides the appropriate line thickness and spacing can be used. Code 39 and Code 128 are among the preferred bar code systems.

Figure 2B:
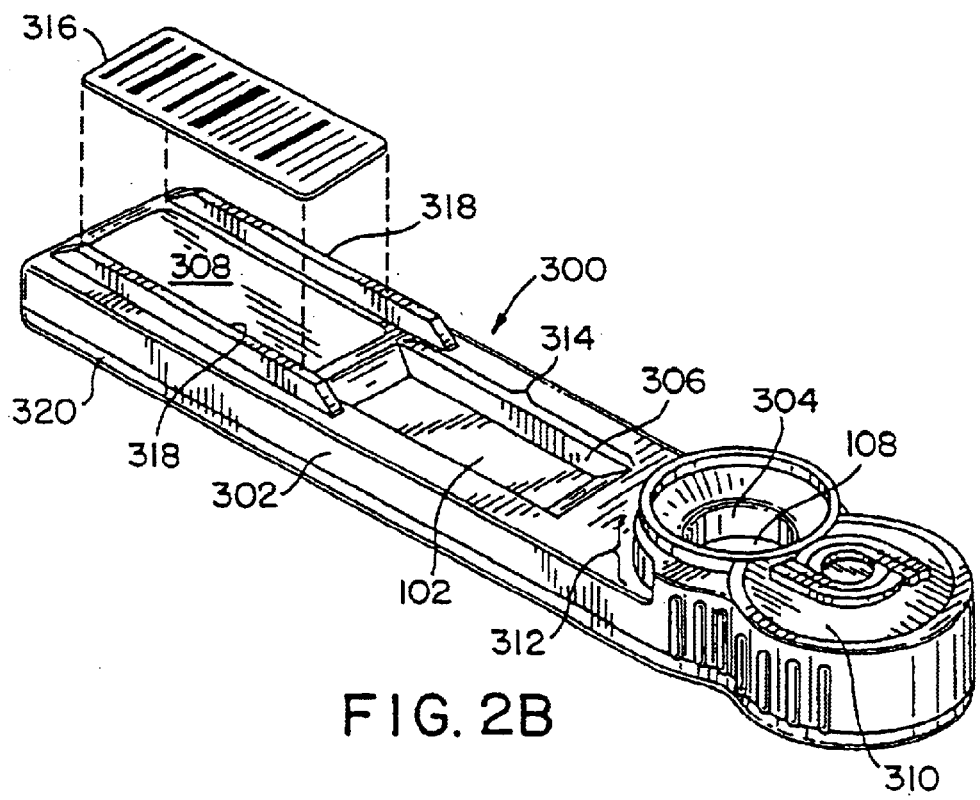
FIG. 2B is a perspective view of an alternative embodiment of an assay device, including the assay test strip of FIG. 1A and FIG. 1B and housing assembly and showing a bar code, which can optionally be affixed to the housing.
Figure 3:
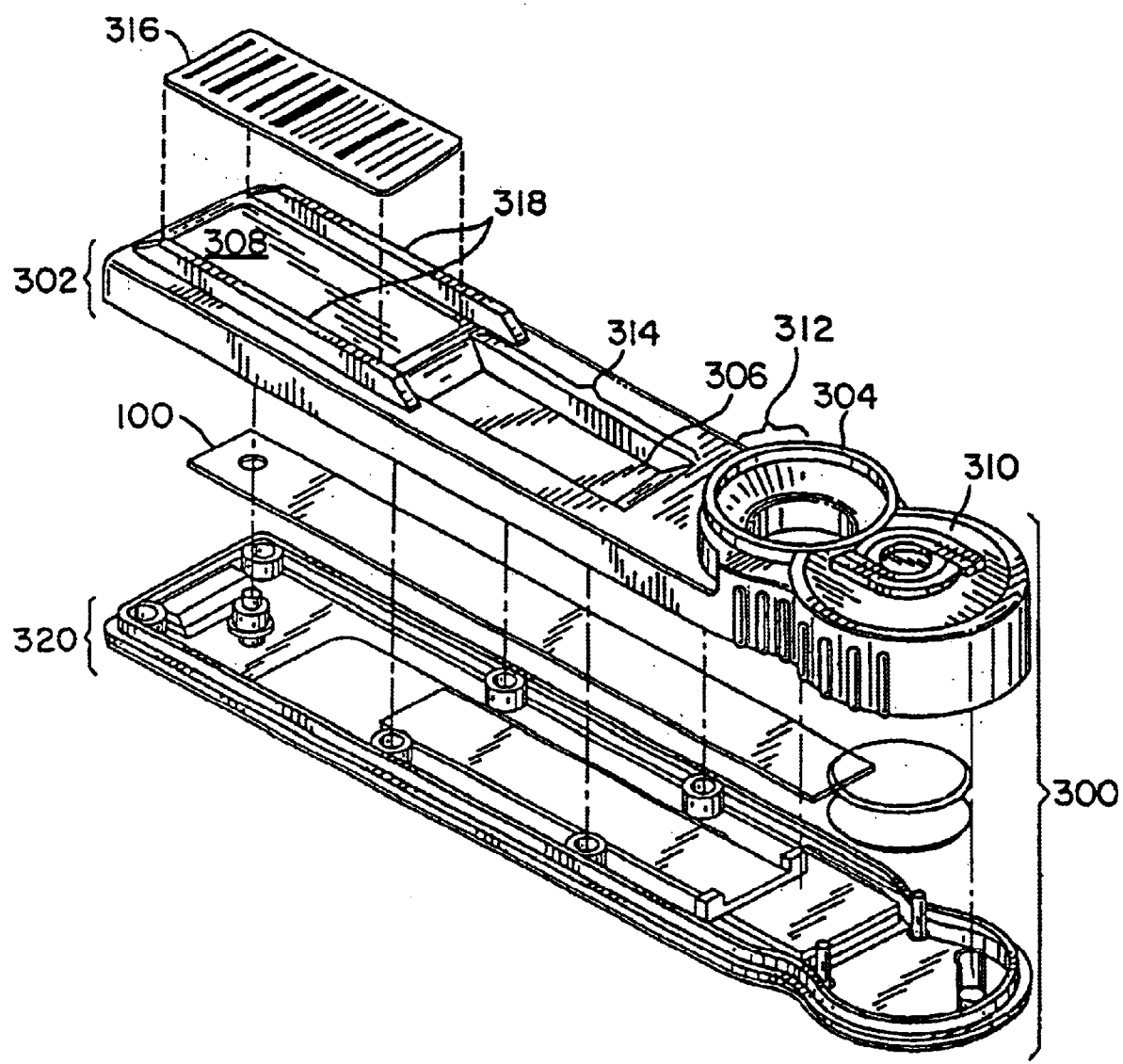
FIG. 3 is a perspective view of the assay device of FIG. 2B showing the individual components of the device.
Figure 25:
FIG. 25 is an example of a bar code in accordance with an exemplary embodiment of the assay device.

In a particular embodiment, Code 39 is used. An example bar code is shown in FIG. 25. The bar code is made up of 11 alphanumerics, including 2 alphabetic and 9 numeric characters. The first and last characters are asterisks (*), as is standard in the Code 39 system. The lot number is stored as 1 alpha and 4 numeric codes so that product complaints or questions can be traced to a particular lot number. In the exemplified embodiment, the first character represents the month of production, the second is a digit representing the year of production and the last three are an index value indicating the lot number. Thus, the lot number "A8001" represents the first device in a lot produced in January, 1998. The next two characters ("01") represent the identity of the analyte as 2 numerics (00–99). This permits the use of up to 100 different analytes with the system. The reflectance intensity value (00–99) is stored as the next two numeric characters ("01"). The intensity value sets the reference threshold for which controls and patient samples can be compared. This eliminates the need to run liquid reference samples on a daily basis. FIGS. 2A, 2B, and 3 depict assay devices that optionally include bar codes, 216 and 316, respectively. Finally, the cassette expiration date is stored as 1 alpha and 1 numeric code to prevent the use of expired devices. In the example given, an expiration code of "A9" represents an expiration date of January, 1999.

Antibodies

Any antibody, including polyclonal or monoclonal antibodies, or any fragment thereof, such as the Fab fragment, that binds the analyte of interest, is contemplated for use herein. Monoclonal and/or polyclonal antibodies may be used. For example, a mouse monoclonal anti-fetal fibronectin antibody may be used in a labeled antibody-conjugate for detecting fetal fibronectin, and a polyclonal goat anti-mouse antibody may also be used to bind fetal fibronectin to form a sandwich complex. An antibody that binds to the labeled antibody conjugate that is not complexed with fetal fibronectin may be immobilized on the test strip and used as a control antibody. For example, when fetal fibronectin is the analyte, a polyclonal goat anti-mouse IgG antibody may be used.

Conjugation of the Antibody to a Label

An antibody conjugate containing a detectable label may be used to bind the analyte of interest. The detectable label used in the antibody conjugate may be any physical or chemical label capable of being detected on a solid support using a reader, preferably a reflectance reader, and capable of being used to distinguish the reagents to be detected from other compounds and materials in the assay.

Suitable antibody labels are well known to those of skill in the art. The labels include, but are not limited to enzyme-substrate combinations that produce color upon reaction, colored particles, such as latex particles, colloidal metal or metal or carbon sol labels, fluorescent labels, and liposome or polymer sacs, which are detected due to aggregation of the label. A preferred label is a colored latex particle. In an alternative embodiment, colloidal gold is used in the labeled antibody conjugate.

The label may be derivatized for linking antibodies, such as by attaching functional groups, such as carboxyl groups to the surface of a particle to permit covalent attachment of antibodies. Antibodies may be conjugated to the label using well known coupling methods. Coupling agents such as glutaraldehyde or carbodiimide may be used. The labels may be bonded or coupled to the antibodies by chemical or physical bonding. In a preferred embodiment, a carbodiimide coupling reagent, 1-ethyl-3-(3-dimethylaminopropyl) carbodiimide (EDAC), is used to link antibodies to latex particles.

Measurement of Analytes

Any analyte that can be detected in any assay, particularly colorimetric assays, including immunoassays and that can be associated with a disorder is contemplated for use as a target herein. Suitable analytes are any which can be used, along with a specific binding partner, such as an antibody, or a competitor, such as an analog, in an assay. Analytes may include, but are not limited to proteins, haptens, immunoglobulins, enzymes, hormones (e.g., hCG, LH, E-3-G estrone-3-glucuronide and P-3-G (progestrone-3-glucuronide)), polynucleotides, steroids, lipoproteins, drugs, bacterial or viral antigens, such as *Streptococcus, Neisseria* and *Chlamydia*, lymphokines, cytokines, and the like. A number of suitable analytes are described in U.S. Pat. No. 5,686,315, which is incorporated herein by reference. Although examples are provided for the determination of fetal fibronectin in cervicovaginal samples, the systems and methods provided herein are not limited to the detection and measurement of fetal fibronectin, but apply to any biochemical test, particularly those for which test strips can be developed or for which test strips are known.

Measurement of Fetal Fibronectin

In an exemplary embodiment, the system is used for diagnosing or predicting conditions such as pregnancy, including ectopic pregnancy, pre-eclampsia, preterm labor or imminent delivery and fetal membrane rupture. Fetal fibronectin is a fetal restricted antigen found in placenta, amniotic fluid and fetal connective tissue. Since fetal fibronectin is strictly associated with pregnancy, determination of the presence of fetal fibronectin in a cervicovaginal sample is a highly reliable early indication of pregnancy. Also, the absence of a fetal restricted antigen in a cervicovaginal sample during the first 20 weeks of pregnancy is an indicator of ectopic pregnancy. Ectopic pregnancies, which are a major cause of mortality for women, are not readily distinguished from normal pregnancies using standard pregnancy determination methods and tests. Determination of impending preterm births is critical for increasing neonatal survival of preterm infants. The presence of fetal fibronectin (fFN) in cervicovaginal secretion samples in patients after week 12 of pregnancy is associated with a risk of impending delivery, including spontaneous abortions (12–20 weeks), preterm delivery (20–37 weeks), term (37–40 weeks) and post-date delivery (after 40 weeks), in pregnant women. In addition, the presence of fetal fibronectin in a cervicovaginal sample provides a method for determining increased risk of labor and fetal membrane rupture after week 20 of pregnancy. Detection of rupture of the amniotic membrane is important in distinguishing true and false labor, and when the rupture is small and the volume of amniotic liquid escaping is small, the rupture is often undetected. The methods; and systems herein provide a means to reliably assess the risk for any of these conditions. An immunoassay procedure for detecting fetal fibronectin is described in EXAMPLE 2.

Test Strip for Measuring fFN and Cellular Fibronectin

Methods for measuring fetal fibronectin and cellular fibronectin levels in cervicovaginal samples are known (see, U.S. Pat. Nos. 5,096,830, 5,185,270, 5,223,440, 5,236,846, 5,281,522, 5,468,619 and 5,516,702, each of which is incorporated herein by reference in its entirety), and diagnostic tests for various pregnancy-related disorders are available (see, e.g., U.S. Pat. Nos. 5,096,830, 5,079,171). These methods can be adapted for use with the immunoassay test strips and devices described herein. In particular, an immunoassay test strip for measuring fFN in cervicovaginal samples is provided.

Antibodies for Fetal Fibronectin

An antibody that will bind the analyte of interest is conjugated to a detectable label. In a particular embodiment, where fetal fibronectin is to be detected, a mouse monoclonal anti-fFN antibody (see, U.S. Pat. No. 5,281,522), conjugated to latex particles containing a blue dye may be used. In an alternative embodiment, a goat polyclonal antibody to human fibronectin is conjugated to a colloidal gold label.

In a preferred embodiment, an antibody that binds the labeled antibody conjugate that is not complexed with fetal fibronectin is used as a control antibody. For example, where the labeled conjugate includes a monoclonal anti-fetal fibronectin antibody, a polyclonal goat anti-mouse IgG antibody is used.

The antibodies may be raised and purified using methods known to those of skill in the art or obtained from publicly available sources. For example, monoclonal antibody FDC-6 (deposited at the American Type Culture Collection as accession number ATCC HB 9018; see U.S. Pat. No. 4,894,326; see, also, Matsuura et al. (1985) *Proc. Natl. Acad. Sci. U.S.A.* 82:6517–6521; see, also, U.S. Pat. Nos. 4,919,889, 5,096,830, 5,185,270, 5,223,440, 5,236,846, 5,281,522, 5,468,619 and 5,516,702), which is raised against whole molecule onco-fetal fibronectin from a tumor cell line, may be used.

Fetal Fibronectin Assay Procedure

In conducting the assay, a patient sample is obtained. The sample may include fluid and particulate solids, and, thus, can be filtered prior to application to the assay test strip. The sample may be removed from the patient using a swab having a fibrous tip, an aspirator, suction or lavage device, syringe, or any other known method of removing a bodily sample, including passive methods for collecting urine or saliva. In particular, the sample may be extracted into a buffer solution, and optionally heated, for example, at 37° C. and filtered. In a preferred embodiment, where fetal fibronectin is to be detected in a sample, the sample is obtained from in the vicinity of the posterior fornix, the ectocervix or external cervical os using a swab having a dacron or other fibrous tip.

A volume of the test sample is then delivered to the test strip (FIGS. 1A and 1B) using any known means for transporting a biological sample, for example, a standard plastic pipet. Any analyte in the sample binds to the labeled antibody, and the resulting complex migrates along the test strip. Alternatively, the sample may be pre-mixed with the labeled conjugate prior to applying the mixture to the test strip. When the labeled antibody-analyte complex encounters a detection zone of the test strip, the immobilized antibody therein binds the complex to form a sandwich complex, thereby forming a colored stripe.

Any unbound latex-conjugated antibody continues to migrate into a control zone where it is captured by a second immobilized antibody or other agent capable of binding the conjugate, and thereby forms a second colored stripe due to the aggregation of the dye-containing latex beads. This indicates that the assay run has been completed.

The results of the assay are assessed using the reader and software provided herein. The rapid test herein provides, at the very least, the same clinically relevant information as a fFN ELISA (an enzyme linked immunosorbent sandwich assay (ELISA) see, e.g., U.S. Pat. No. 5,281,522) test heretofore available, but in significantly less time and at the point of care. This rapid fFN immunoassay allows the user to test a cervicovaginal swab sample in about 20 minutes. When comparing the 20 minute rapid fFN test to the data from the fFN ELISA, a Kappa coefficient of 0.68 was found with a 95% confidence interval [0.62, 0.76] and an overall concordance of at least about 91.6%. These data were obtained using a system including an immunoassay test strip in combination with a reflectance reader and data processing software employing data reduction and curve fitting algorithms or neural networks, as described herein. Thus, the systems herein provide results that are at the very least comparable to the ELISA, but generally are superior and more informative.

Reader

Reflectance and other readers, including densitometers and transmittance readers, are known to those of skill in the art (see, e.g., U.S. Pat. Nos. 5,598,007, 5,132,097, 5,094,955, 4,267,261, 5,118,183, 5,661,563, 4,647,544, 4,197,088, 4,666,309, 5,457,313, 3,905,767, 5,198,369, 4,400,353). Any reader that upon combination with appropriate software, as described herein, can be used to detect images and digitize images, such as symbologies, particularly bar codes or the lines and stripes produced on chromatographic immunoassay devices or on gels or photographic images thereof, such as the lines on DNA and RNA sequencing gels, X-rays, electrocardiograms, and other such data, is intended for use herein.

The reader provided herein, particularly in combination with the software provided herein, is preferred for use in the point of care diagnostic systems.

In an exemplified embodiment, a sample is applied to a diagnostic immunoassay test strip, and colored or dark bands are produced. The intensity of the color reflected by the colored label in the test region (or detection zone) of the test strip is, for concentration ranges of interest, directly proportional or otherwise correlated with an amount of analyte present in the sample being tested.

The color intensity produced is read, in accordance with the present embodiment, using a reader device, for example, a reflectance reader, adapted to read the test strip. The intensity of the color reflected by the colored label in the test region (or detection zone) of the test strip is directly proportional to the amount of analyte present in the sample being tested. In other words, a darker colored line in the test region indicates a greater amount of analyte, whereas a lighter colored line in the test region indicates a smaller amount of analyte. In accordance with the present embodiment, the color intensity produced, i.e., the darkness or lightness of the colored line, is read using a reader device, for example, a reflectance reader, adapted to read the test strip. A reflectance measurement obtained by the reader device is, in accordance with the present embodiment, correlated to the presence and/or quantity of analyte present in the sample as described hereinbelow. The reader takes a plurality of readings along the strip; and obtains data that are used to generate results that are an indication of the presence and/or quantity of analyte present in the sample as described hereinbelow. The system also correlates such data with the presence of a disorder, condition or risk thereof.

Optionally, in addition to reading the test strip, the reader may be adapted to read a symbology, such as a bar code, which is present on the test strip or housing and encodes information relating to the test strip device and/or test result and/or patient, and/or reagent or other desired information. Typically the associated information is stored in a remote computer database, but can be manually stored. In other embodiments, the symbology can be imprinted when the device is used and the information encoded therein.

Figure 6:
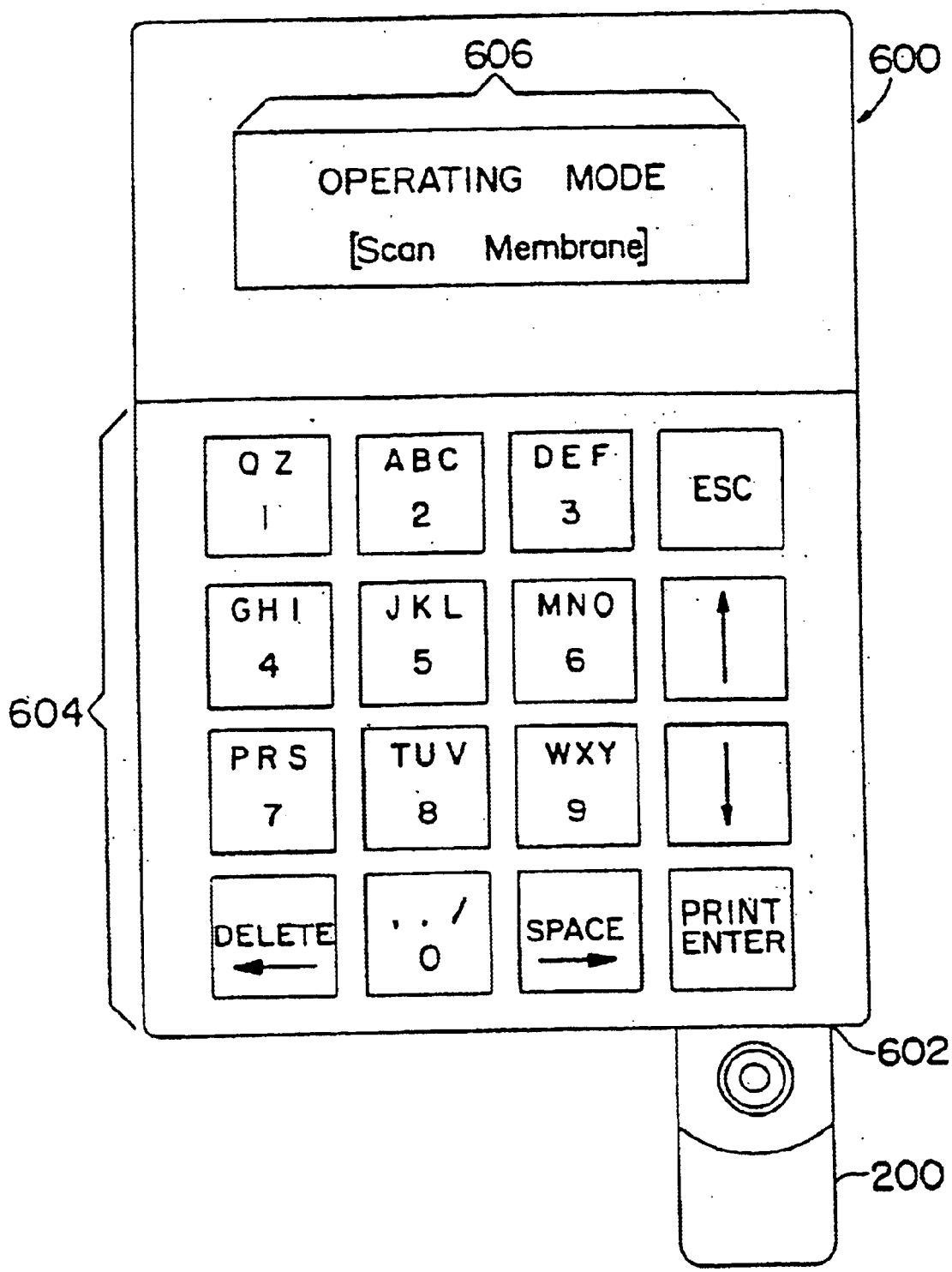
FIG. 6 is a top view of an embodiment of an assay reader and an assay device, inserted therein, in accordance with an exemplary embodiment of the reader.

Referring to FIG. 6, an exemplary embodiment of the reader device 600 is shown with an immunoassay device 200, as shown in FIG. 2A, inserted into a cassette slot 602 therein. The cassette slot 602 is adapted to receive the immunoassay device 200, and a reader head assembly (not shown) supported within the reader device 600 is adapted to read the immunoassay test strip, and optionally a symbology, exemplified as a bar code with on the immunoassay device. Such reading is performed by scanning a reader head (not shown) across the device, including a test window 214 in the immunoassay device 200 and a symbology, such as the exemplified bar code 216, if present, and in the process directing light onto the bar code and/or a test portion and a control portion of the immunoassay test strip. An amount of such light reflected back from the bar code and/or the test portion and control portion of the immunoassay test strip is measured as the reader head scans across the device.

Also shown are a data entry keypad 604, including ten digit keys (also labeled with letters of the alphabet, such as is commonly the case on telephone keypads), a delete key, a space key, an escape key, a print key, enter key, and up, down, left and right arrow keys, additional characters such as , or . or /, and any others desired by the user. The data entry keypad 604 can be used by an operator of the reader device 600 to input identification information, to enter control test parameters, to initiate and terminate testing, and the like. A processing unit (not shown) housed within the reader device 600 is responsive to the keypad and performs data analysis functions, as described hereinbelow, in accordance with modifications made to a processor in the processing unit by an appropriate software subsystem.

Also shown in FIG. 6 is a liquid crystal display screen 606. The liquid crystal display screen 606 receives output data from the processing unit and displays it to an operator of the reader device 600, including displaying results of tests, error messages, instructions, troubleshooting information, and the like.

Figure 7:
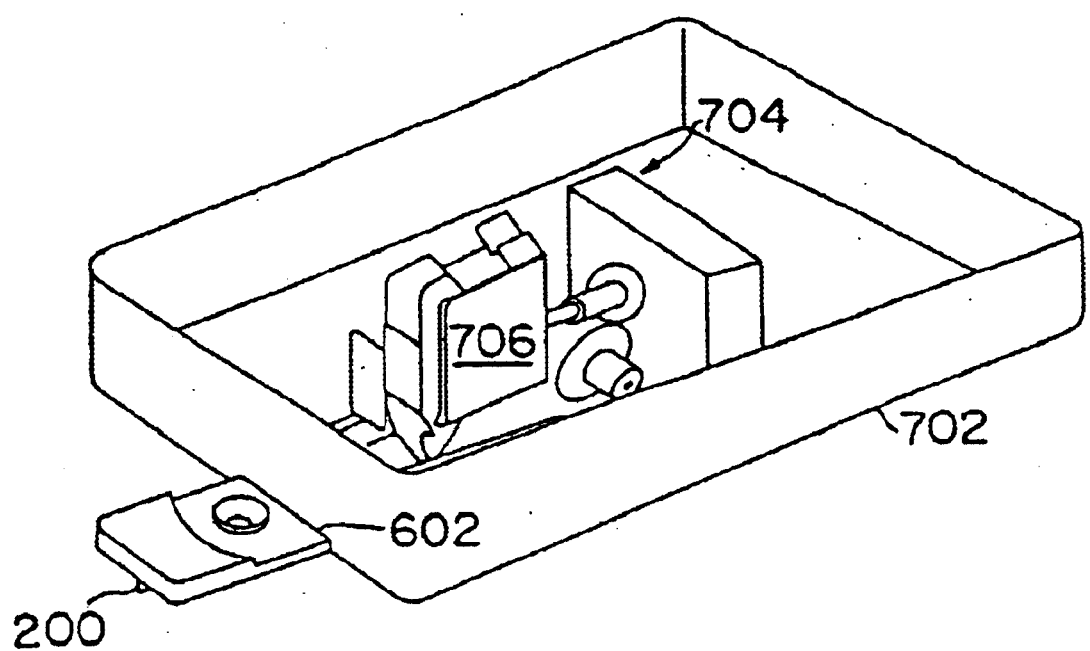
FIG. 7 is a perspective view of portion of the assay device of FIG. 2A shown inserted into a cassette slot of a lower housing and extending to a reader head assembly within an exemplary embodiment of an assay reader.

Referring next to FIG. 7, a perspective view of a lower housing 702 of one embodiment of an immunoassay reader device 600 of FIG. 6 is shown with a reader head assembly 704 located therein and the immunoassay device 200 inserted into the cassette slot 602 at a front edge of the lower housing 702. The cassette slot 602 located at the front edge of the lower housing 702 provides an aperture through which the immunoassay device 200 is inserted into and guided into the reader device 600 in order measure light reflected from an immunoassay test strip. In some embodiments of the reader, the reader is adapted to additionally read a symbology, such as a bar code, imprinted, engraved on or otherwise affixed to the test strip or device.

When the immunoassay device 200 is inserted into the cassette slot 602 of the lower housing, a reader head 706 on the reader head assembly 704 is positioned directly above the device 200, such that the longitudinal (or major) axes of optical fibers within the reader head 706 are normal to a surface of the device, including the test strip and optionally a symbology that is imprinted, engraved or other wise affixed on the device.

Alternatively, the reader head 706 may be fixed, at least rotationally, and the immunoassay device 200 may be moved into position after insertion into the cassette slot 602, such that the longitudinal (or major) axes of optical fibers within the reader head 706 are normal to a surface of the device to be read by the reader.

Figure 8:
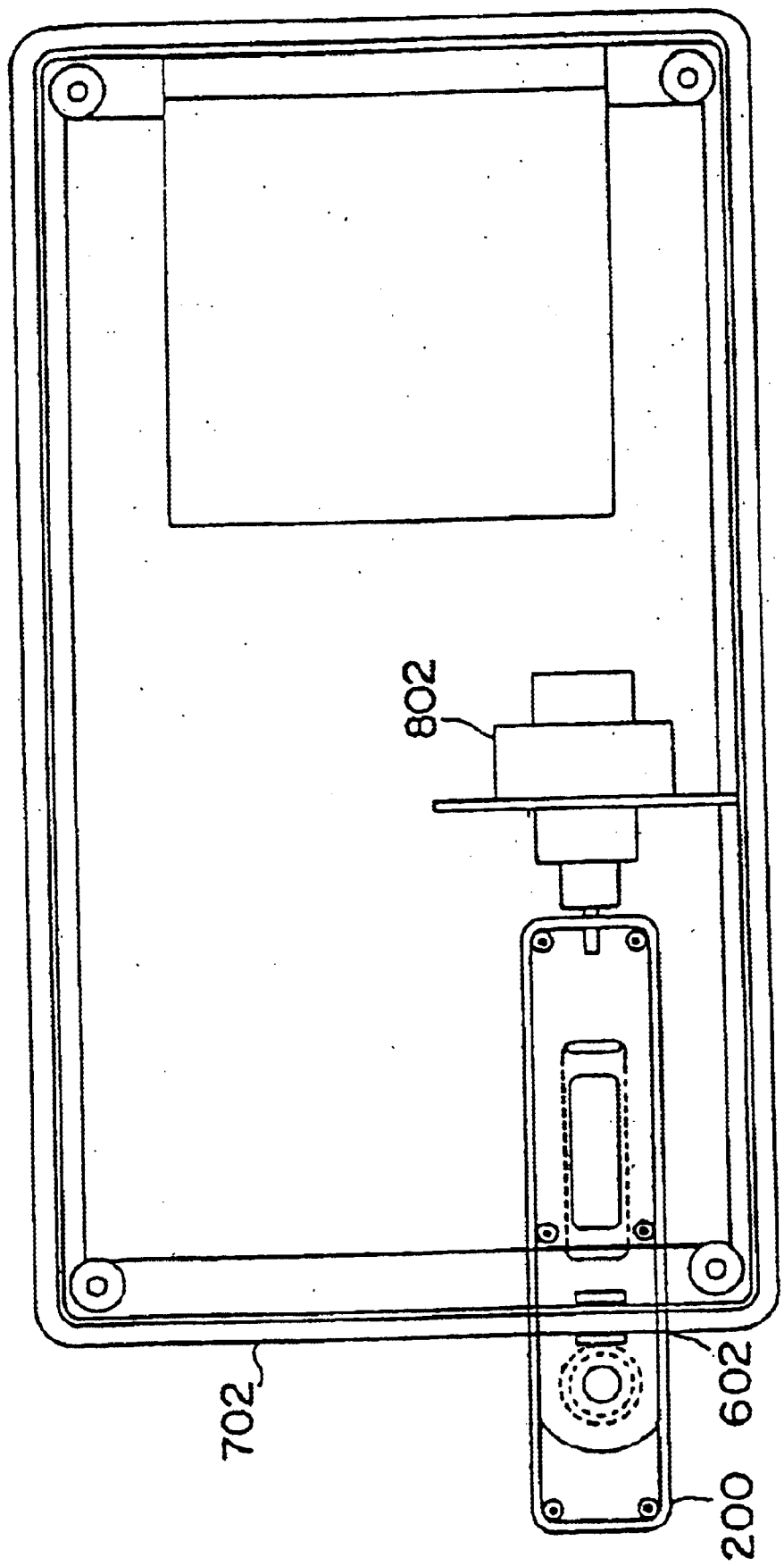
FIG. 8 is a top view of the lower housing of the assay reader of FIG. 7 with the assay device inserted therein and a stepper motor shown positioned relative to the assay device as is when the assay device is fully inserted into the cassette slot of the reader.

Referring next to FIG. 8, a top view is shown of the lower housing 702, the immunoassay device 200, the cassette slot 602, and a stepper motor 802. As can be seen, after insertion into the lower housing 702, the immunoassay device 200 is positioned in alignment with the stepper motor 802, which is part of the reader head assembly. The stepper motor is used to scan the reader head 706 across the symbology, such as the exemplified bar code 216 and/or test window 214 of the immunoassay device 200.

Figure 9:
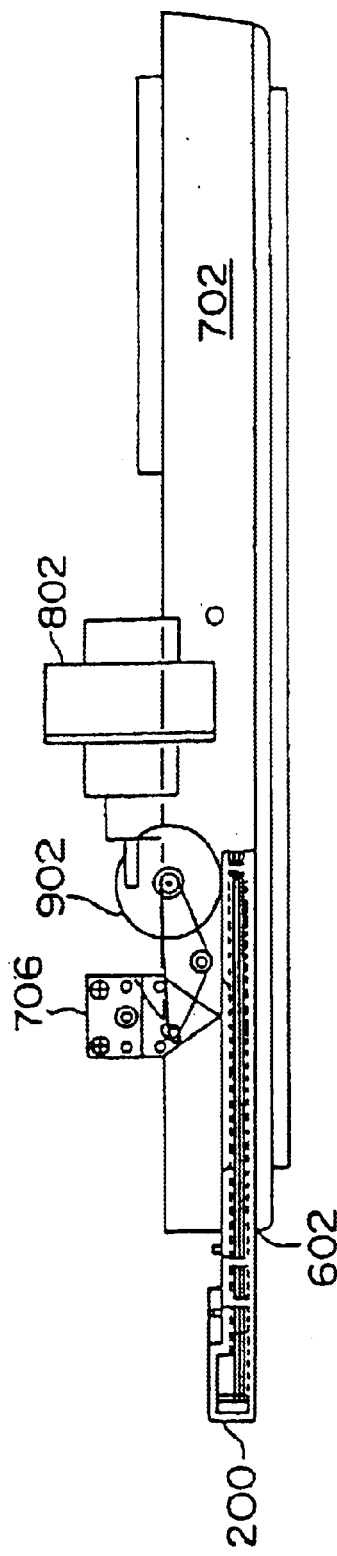
FIG. 9 is a side view of the lower housing of the reader device of FIG. 7 with the assay device of FIG. 2A fully inserted with the stepper motor shown positioned relative to the fully inserted assay device, with a reader head shown positioned in a lowered position over a test opening of the assay device, and with a carriage wheel shown engaged by the assay device so as to lower the reader head into its lowered position therein.

One embodiment of the reader device is shown in FIG. 9. Shown are the lower housing 702, the immunoassay device 200, the stepper motor 802, an actuator wheel 902, the reader head 706, and linkages for moving the reader head 706 parallel to a major axis of the immunoassay device 200 in order to scan the reader head 706 across the symbology (bar code) 216 and/or test window 214 of the immunoassay device 2090.

To read the immunoassay test strip, the reader head is brought within a uniform distance of about 0.010 inches from the test strip. When the immunoassay device 200 is slid into the cassette slot 602, the actuator wheel 902 and an actuator spring (not shown) work together to bring the reader head 706 down to within about 0.010 inches of the immunoassay test strip within the housing 202 of the immunoassay device 200. In order to move the reader head 706 into position within, 0.010 inches of the immunoassay test strip, the reader head 706 is pivoted along with a portion of the reader head assembly. Prior to being brought into position within 0.010 inches of the immunoassay test strip, while the immunoassay device 200 is being inserted into or removed from the immunoassay reader device 600, the reader head 706 assumes a retracted position, i.e., raised position, so that the immunoassay device 200 can be inserted into or removed from the immunoassay reader device 600 without crashing the reader head 706 into the immunoassay device 200.

When the immunoassay device 200 is inserted into the cassette slot 602, it contacts the actuator wheel 902 and causes a carriage assembly of the reader head assembly to be brought down from the retracted position so that the reader head 706 is within 0.010 inches of the immunoassay test strip.

Insertion of the immunoassay device 200 causes the actuator wheel to pop-up by applying pressure to the actuator spring, bringing the carriage assembly down from the retracted position.

The immunoassay device 200 is pushed into the cassette slot 602 until it meets a stop. Once inserted, the immunoassay device 200, the actuator wheel 902, and the actuator spring remain fixed in position, while the reader head 706 is stepped across the test window 214 of the immunoassay device 200 by the stepper motor 802. In other words, only the reader head 706 moves during the scanning of the immunoassay test strip.

Alternatively, the immunoassay device 200 is pushed into the cassette slot 602 until it meets the stop. Once inserted the immunoassay device 200 may be rotated up to within 0.010 inches of the reader head 706 by gently lifting the immunoassay device 200. By gently lifting the immunoassay device 200, a base of the reader head assembly is pivoted up toward the carriage assembly and the reader head 706, positioning the immunoassay test strip within 0.010 inches of the reader head 706 the reader head 706 is then stepped across with test window 214 of the immunoassay test strip by the stepper motor 802. In other words, in accordance with this alternative, only the reader head 706 moves during the scanning of the immunoassay test strip/and; the reader head 706 moves only during the scanning of the immunoassay test strip.

Prior to insertion of the immunoassay device 200 into the cassette slot 602, and prior to scanning, the reader head 706 is positioned at a point that would place it approximately half way across (in the middle of) the test window 214 of the immunoassay device 200. After insertion of the device 200 into the reader 600, when an operator depresses a scan key on the key pad (see FIG. 6), the reader head 706 is moved from this position toward the stepper motor 802 until a microswitch is activated. Once the microswitch is activated, the reader head 706 is said to be in a "home" position from which scanning of the test strip commences. Once scanning commences, the reader head 706 advances from the home position across the test window 214. Thus, the reader head 706 scans in a direction moving away from the stepper motor toward the cassette slot 602 or to the left as depicted in FIG. 9. Total travel of the reader head 706 during scanning of the immunoassay test strip is 0.452 inches, which is achieved in 0.002 inch steps, which are 226 in number. One set of readings is taken per step, with each set of readings including a dark reading, a first light reading and a second light reading.

Figure 10:
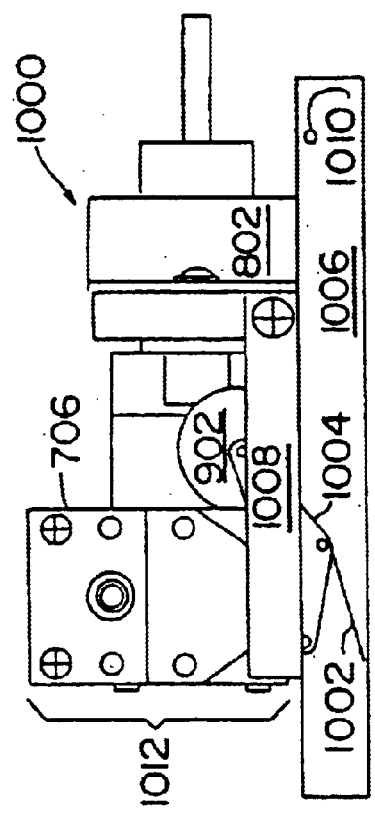
FIG. 10 is a side view of a reader head assembly such as is found in the reader device of FIG. 6.

Referring next to FIG. 10, the reader head assembly 1000 is shown. Shown are the actuator spring 1002, the actuator 1004, the base 1006, the stepper motor 802, the actuator wheel 902, a rotor arm 1008, and the reader head 706. Also shown is a pivot point 1010 on which the carriage assembly 1012, including the reader head 706, stepper motor 802, actuator wheel 902, actuator spring; 1002, and rotor arm 1008 pivot to assume a raised position for insertion and removal of the immunoassay device 200 from the reader device 600 and to assume a lowered position for scanning the reader head 706 across the test window 214 of the immunoassay device 200.

Figure 11:
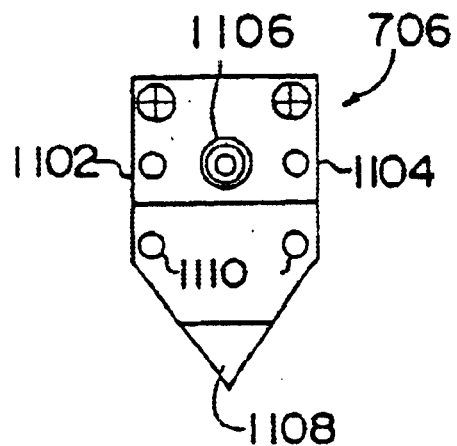
FIG. 11 is a side view of a reader head of the reader head assembly of FIG. 10.

Referring next to FIG. 11, shown is a side view of the reader head 706 of the reader head assembly of FIG. 10. Shown is a first light emitting diode (LED) 1102, a second light emitting diode (LED) 1104, a photodetector 1106, a reader head aperture 1108, and mounting holes 1110.

Figure 12:
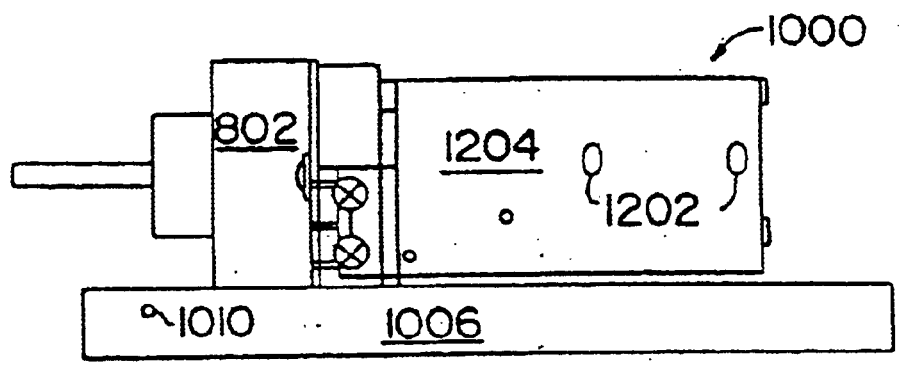
FIG. 12 is a reverse angle side view of the reader head assembly of FIG. 10.

Referring next to FIG. 12 a reverse angle side view is shown of the reader head assembly 1000 of FIG. 10. Shown are the stepper motor 802, the base 1006, mounting holes 1202, and a mounting bracket 1204 on which the reader head 706 is mounted.

Figure 13:
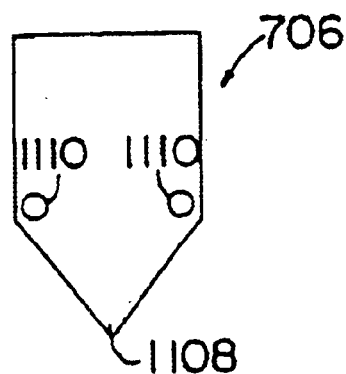
FIG. 13 is a reverse angle side view of the reader head of FIG. 11.

Referring next to FIG. 13 a reverse angle side view of the reader head 706 of FIG. 11 is shown. Seen are the mounting holes 1110, and the reader head aperture 1108.

Figure 14:
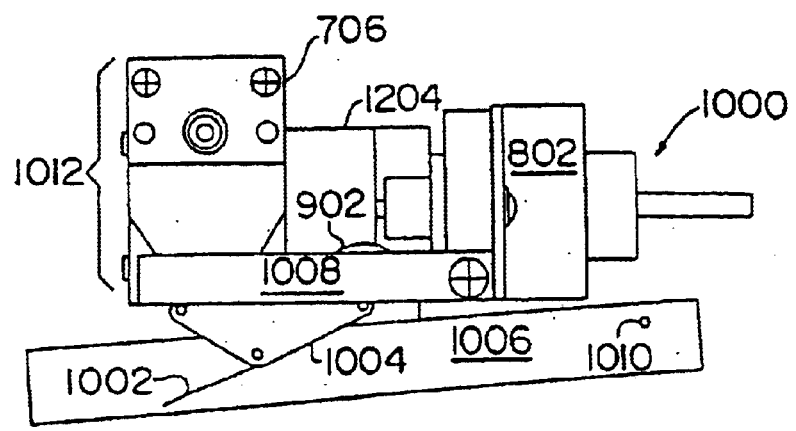
FIG. 14 is a side view of the reader head assembly of FIG. 10, having been actuated so as to pivot the reader head assembly into a raised position suitable for insertion and removal of the assay device into and from the reader head assembly within the assay reader.

Referring next to FIG. 14, shown is a side view of the reader head assembly 1000 of FIG. 10 having assumed a retracted position. Shown are the actuator spring 1002, the actuator arm 1004, the stepper motor 802, the reader head 706, the reader head supporting bracket 1204, the pivot 1010 on which such elements rotate, and a base 1006 relative to which such elements rotate.

As can be seen, the actuator arm 1004, the actuator spring 1002, the stepper motor 802, the reader head 706, the reader head mounting bracket 1204, and mechanisms used for supporting and scanning the reader head 706 are designed so that the test strip 100 in the device 200 is positioned within 0.010 inches of the aperture 1108 of the reader head. Any design suitable to effect such can be employed with the present embodiment.

In the example illustrated, the actuator arm 1004, the actuator spring 1002, the stepper motor 802, the reader head 706, the reader head mounting bracket 1204, and the mechanisms used for supporting and scanning the reader head 706 are shown rotated on the pivot 1010 such as would be the case, in accordance with the variation shown, when the immunoassay device 200 has been removed from the reader, device 600 and/or as the immunoassay device 200 is being inserted into or removed from the reader device 600.

Figure 15:
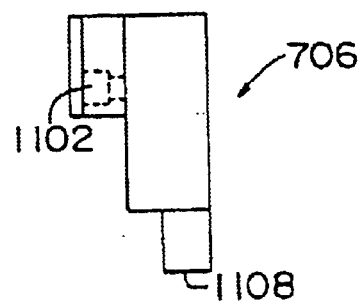
FIG. 15 is an end view of the reader head of FIG. 11.

Referring next to FIG. 15, a side view is shown of the reader head 706 of FIG. 11. Shown are the aperture 1108 and the first light emitting diode 1102.

Figure 16:
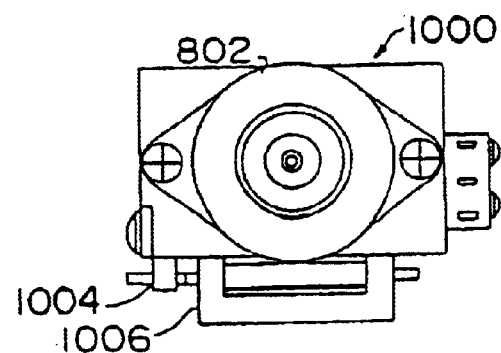
FIG. 16 is an end view of the reader head assembly of FIG. 10.

Referring next to FIG. 16, an end view is shown of the reader head assembly 1000 of FIG. 10. Shown is the stepper motor 802, the base 1006, and the actuator arm 1004.

Figure 24:
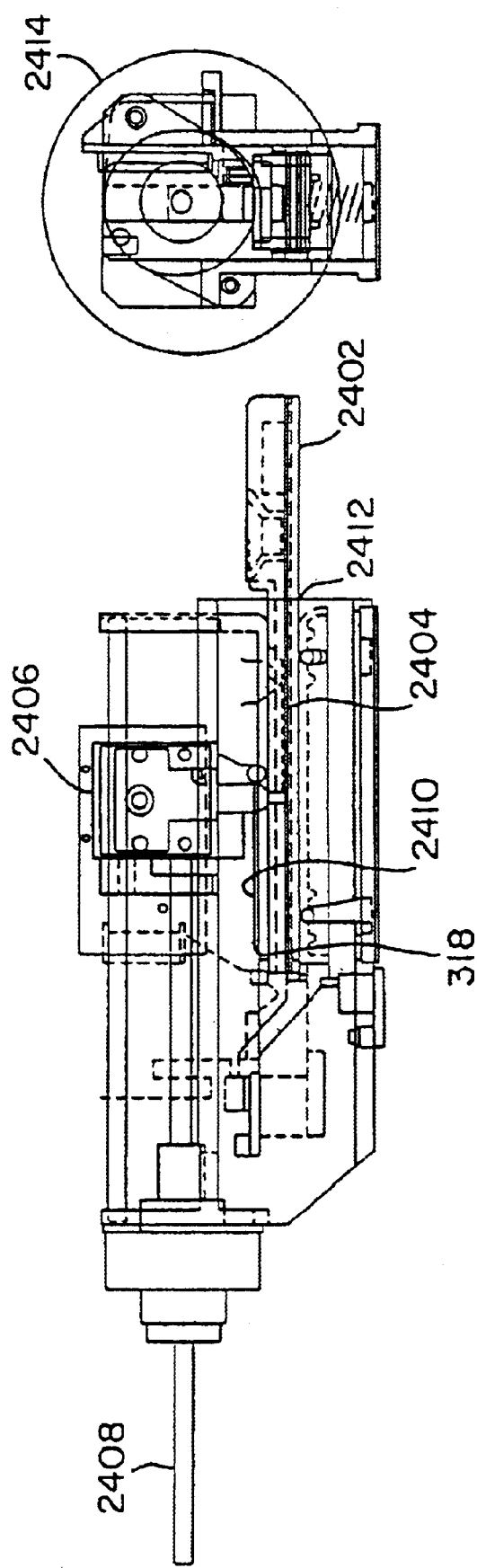
FIG. 24 is a side view of an exemplary embodiment of the reader that is adapted for reading a bar code.

In alternative embodiments, the reader is adapted to read a symbology, such as a bar code. An exemplary embodiment of a reader so-adapted is shown in FIG. 24. In this embodiment, when the device, cassette 2402 is inserted into the reader, it sits on a spring stage 2404. Prior to insertion of the device 300 (as shown in FIG. 2B) into the cassette slot 602, and prior to scanning, the reader head 2406 is positioned at a point that would place it approximately 0.125 inches from the forward edge of the device as it is inserted into the reader.

As shown in FIG. 2B, the device includes guide ridges 318 on either side of the bar code along the outer edges of the upper surface of the device. The reader head 2406 is moved by the shaft 2408 of the stepper motor 2414 and scans in a direction moving away from the stepper motor toward the cassette slot 2412. As the reader head 2406 moves along the device above the bar code 2410, the guide ridges 2412 contact the reader head assembly and act to compress the spring stage 2404 by 3° in order maintain the reader head 2406 at a distance of 0.010 inches above the bar code 2410 as the bar code 2410 is read. After the bar code 2410 is read, the reader head assembly 2406 moves off the guide ridges 2412, the spring stage 2404 returns to a level position (0°), and the reader head 2406 is repositioned at a distance of 0.010 inches in order to read the test strip. When reading a symbology, such as a bar code, the reader is moved in steps of approximately between 0.002–0.008 inches at a scan resolution of approximately 125–500 steps per inch, preferably about 250 steps per inch. One set of readings is taken per step, with each set of readings including a dark reading, a first light reading and a second light reading.

Regardless of whether one of these alternatives is used, or whether any of numerous variations thereof or any of numerous other possible embodiments well within the abilities of the skilled artisan to easily produce is used in order to position the reader head within a prescribed distance, e.g., 0.010 inches, of the test strip symbology, such as a bar code, a suitable mechanism is preferably employed to effect such positioning.

Figure 17:
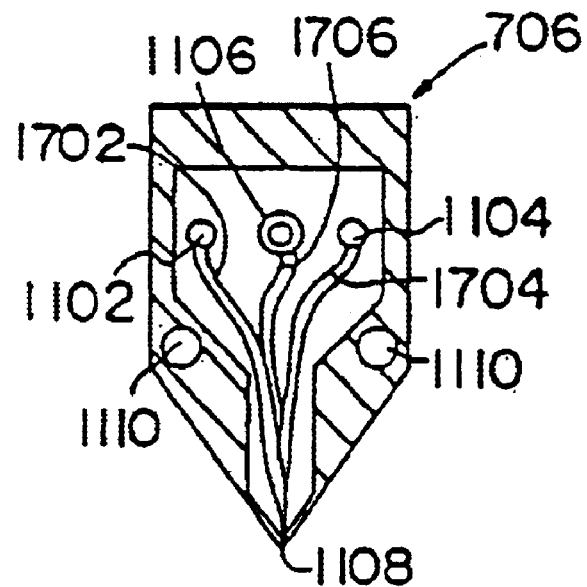
FIG. 17 is a cut-away view of the reader head assembly of FIG. 11 with first and second light emitting diodes, a photodetector, corresponding fiberoptic bundles and an aperture at a lower end thereof depicted.

Referring next to FIG. 17, shown is a side view partially in cross-section of an exemplary embodiment of the reader head. Shown are a first light emitting diode 1102, a second light emitting diode 1104 and a photodetector 1106. Also shown is an aperture 1108 and the mounting holes 1110. Shown coupled between each of the LED's 1102, 1104 and the aperture 1108 are first and second fiberoptic bundles 1702, 1704. Similarly, a third fiberoptic bundle 1706 is shown coupled between the aperture 1108 and the photodetector 1106. The first and second fiberoptic bundles 1702, 1704 conduct light from the first and second LED's 1102, 1104, respectively, to the aperture 1108. The third fiberoptic bundle 1706 conducts light from the aperture 1108 to the photodetector 1106. In response to such light, the photodetector generates a reflection signal, e.g., a voltage indicative of an amount of reflected light. The electrical signal can be then processed and converted to a digital signal by using any method commonly known to those of skill in the art.

Figure 18:
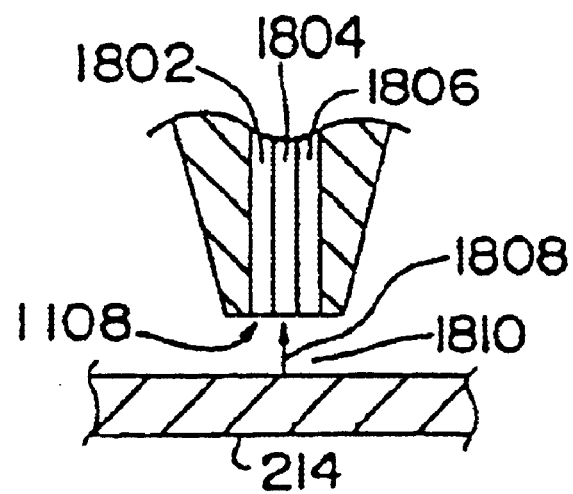
FIG. 18 is a partial closeup cross-sectional view of a reader head tip of the reader head of FIG. 17 showing the aperture and ends of fiberoptic fibers of the fiberoptic bundles of FIG. 17.

Referring next to FIG. 18, shown is a closeup partial cross-sectional view of the aperture 1108 of FIG. 17. Also shown are individual fiberoptic fibers 1802, 1804, 1806 of the fiberoptic bundles 1702, 1704, 1706 of FIG. 17, positioned within the aperture 1108 so as to transmit light 1808 from the aperture 1108 onto the symbology (exemplified bar code) and/or test strip 100 and to receive reflected light 1808 from the bar code and/or test strip 100 entering the aperture 1108. (The transmitted and reflected light 1808 is represented with an arrow.) As can be seen, a gap 1810 between the aperture 1108 and the bar code and/or test strip 100 is present. The gap 1810 preferably has a width of approximately 0.010 inches, which is maintained as the reader head 706 is scanned across the bar code and/or test window 214 of the test strip 100.

Figure 19:
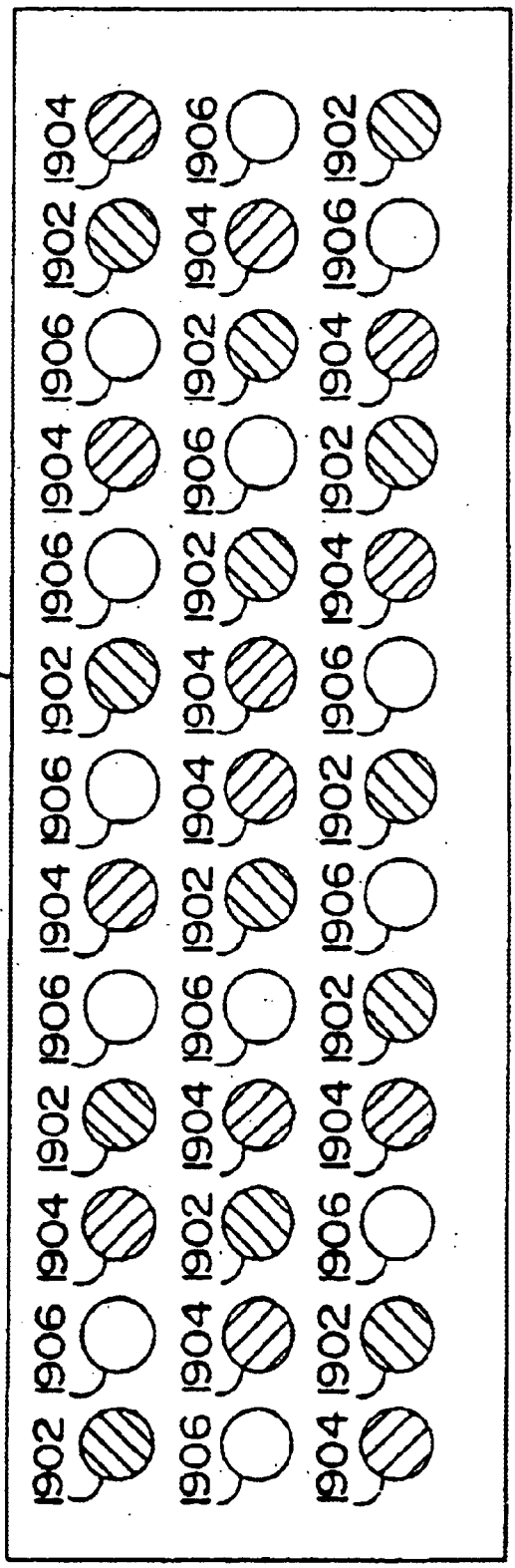
FIG. 19 is a closeup bottom view of the aperture of the reader head of FIGS. 17 and 18 illustrating a sigmoidal pattern for positioning individual fiberoptic fibers (fiberoptic conductors)

Referring next to FIG. 19, a bottom view is shown of individual fiberoptic fiber ends 1902, 1904, 1906 positioned in the aperture 1108 of the reader head 706 of FIG. 10 so as to maximize the distribution of light emitted from individual fiberoptic fibers (fiberoptic conductors), and furthermore to maximize the uniformity of light received into individual fiberoptic conductors. Indicated using diagonal cross-hatching angled from lower left to upper right are individual fiberoptic conductor ends 1902 of the first fiberoptic bundle 1702. These individual fiberoptic conductor ends 1902 carry light emitted from the first light emitting diode from the first fiberoptic bundle through the aperture 1108 of the reader head 706. Similarly, indicated with cross-hatching from an upper left to lower right are fiberoptic conductor ends 1904 of the second fiberoptic bundle 1704. These individual fiberoptic conductor ends carry light emitted from the second light emitting diode to the aperture 1108 of the reader head 706. Without cross-hatching are shown individual fiberoptic conductor ends 1906 of the third fiberoptic bundle 1706. The third fiberoptic bundle 1706 carries light entering the aperture 1108 to the photodetector.

By employing the particularly advantageous arrangement of the fiberoptic conductor ends 1902, 1904, 1906 at the aperture 1108, uniform distribution emissions and light reception is achieved. Such arrangement is said to be a "sigmoidal" (S-like or serpentine) arrangement or a "sigmoidal" distribution. It is an important feature of the present embodiment that the fiberoptic fibers in each of the three groups are arranged along with fiberoptic fibers from the remaining groups in a sigmoidal-like (or "S"-like) pattern with three columns of thirteen fiberoptic fibers each. An arrangement that achieves this feature is intended herein.

In order to achieve the sigmoidal arrangement of fiberoptic conductor ends shown 39 fiberoptic conductors are positioned within the aperture 1108. Next; a clamp assembly made up of a "U"-shaped channel, and an "I"-shaped clamp positioned at the open side of the "U" is employed. The fiberoptic conductors, portions of which protrude from the aperture 1108; are placed between the "U"-shaped channel and the "I"-shaped clamp; and a compressive force is applied thereto by the "I"-shaped clamp, holding the protruding portions of the fiberoptic conductors firmly in position. A resin is then poured into the reader head 706 so as to become interposed between and around the fiberoptic conductors at the aperture 1108. Once the resin is set, the clamp assembly is removed, and the protruding portions of the fiberoptic conductors are trimmed back flush with the aperture 1108, so as to define a planar surface of fiberoptic conductor ends 1902, 1904, 1906 at the aperture 1108. This planar surface is held parallel to a plane at an upper surface of the immunoassay test strip 100 during scanning of the immunoassay test strip.

Advantageously, by creating this planar surface of fiberoptic conductor ends 1902, 1904, 1906, the associated fiberoptic conductors have longitudinal axes that are substantially parallel to one another and normal to the plane defined by the fiberoptic conductor ends 1902, 1904, 1906. As a result, very efficient transfer of light to and from the fiberoptic conductor ends 1902, 1904, 1906 is achieved.

Once the fiberoptic conductor ends 1902, 1904, 1906 are set in the resin, and trimmed, as described above the individual fiberoptic conductors are tested by projecting light individually through the fiberoptic conductors toward the fiberoptic conductor ends 1902, 1904, 1906, to locate the fiberoptic conductor end associated with the particular fiberoptic conductor being tested. This determination is made by observing which of the fiberoptic conductor ends 1902, 1904, 1906 "lights up" when light is transmitted down the particular fiberoptic conductor. As fiberoptic conductors associated with the fiberoptic conductor ends 1902, 1904, 1906 are identified, the fiberoptic conductors are assigned to one of the first, second, and third fiberoptic bundles, so as to achieve, for example, the sigmoidal distribution of fiberoptic conductor ends 1902, 1904, 1906 illustrated in FIG. 19.

Advantageously, by effecting the sigmoidal distribution of fiberoptic conductor ends 1902, 1904, 1906 associated with fiberoptic conductors of each of the first, second, and third fiberoptic bundles, a uniform distribution of light emitted from the aperture 1108, and a uniform distribution of light reflected back to the aperture 1108 is achieved.

Figure 20:
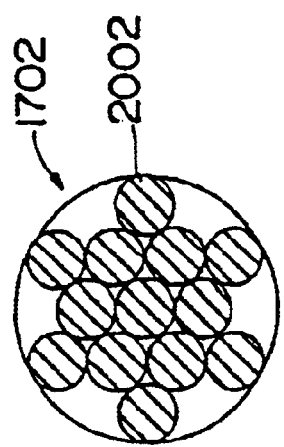
FIG. 20 is a closeup end view of the corresponding fiberoptic bundle at the first light emitting diode of FIG. 17 from which the fiberoptic bundle conducts light from the first light emitting diode.

Referring next to FIG. 20, a cross-sectional view of a first fiberoptic bundle 1702 is shown with individual fiberoptic elements 2002 selected to effect the sigmoidal distribution of FIG. 19. As can be seen, 13 individual fiberoptic elements are present in the fiberoptic bundle 1702, which is the same number of fiberoptic conductor ends 1902, 1904, 1906 depicted in FIG. 19 for each of the three fiberoptic bundles 1702, 1704, 1706. The fiberoptic bundle 1702 shown in FIG. 17 carries the light from the first light emitting diode to the aperture 1108 of the reader head 706. Cross-sectional views of the second and third fiberoptic bundles are similar to that shown in FIG. 20.

Referring next to FIGS. 21, 22 and 23, three schematic views are shown illustrating a process for reading test results from immunoassay test strip 100 with the control region 2102 and the detection region 2104 depicted thereon. In the example shown, blue latex particles are detected in the test region and the control region on a nitrocellulose support. Also depicted are the aperture 1108 of the reader head 706 in a dark reading mode (FIG. 21), a first light reading mode (FIG. 22) and a second light reading mode (FIG. 23).

The reader head assembly (described above) includes the first light-emitting diode (which in the present example is a blue LED), the second LED (which in the present example is an amber LED), a silicon photodiode detector, and fiberoptic fibers arranged with fiberoptic conductor ends 1902, 1904, 1906 in the sigmoidal distribution in the aperture 1108 (e.g., 0.002 inches wide), which is located at the bottom (or tip) of the reader head 706 at a point nearest the immunoassay test strip, when the immunoassay device is inserted into the immunoassay reader device. It is understood that the selection of LEDs will be dependent upon the signal produced in the test; all detectable electromagnetic wavelengths, preferably visible light, are contemplated herein. Fluorescence and other such labeling means are also contemplated herein.

The blue LED and the amber LED emit light of specified wavelengths ($\lambda_1$ and $\lambda_2$, respectively). It should be understood that any suitable wavelengths may be selected. Such selection is dependent on the particular assay with which the immunoassay reader device is being employed. The wavelengths selected are selected so as to allow removal of effects of the background of the immunoassay test strip or symbology, e.g., bar code, from the reflectance readings, and to optimize a reading of a reduction in reflectance associated with accumulated label at the reaction regions of the immunoassay test strip.

In a preferred embodiment, where blue latex particles are detected on a nitrocellulose support, light having a wavelength of 430 nm (blue) is emitted from the first light emitting diode ($LED_1$), i.e., the blue LED, into the first fiberoptic bundle 1702. The same wavelengths can be used to read a symbology, such as a bar code, associated with the assay device. The first fiberoptic bundle 1702 transmits blue light to the aperture 1108 in the reader head 706 where it is emitted at an orientation normal to a plane at the upper surface of the symbology (exemplified bar code) or test strip. A second light emitting diode ($LED_2$), i.e., the amber LED, emits light with a wavelength of 595 nm (amber) into a second fiberoptic bundle 1704. The second fiberoptic bundle 1704 transmits the amber light to the aperture in the reader head 706 where it is emitted at an orientation normal to the plane at the upper surface of the bar code or test strip.

At the aperture, individual fiberoptic conductor ends 1902, 1904 of the first and second fiberoptic bundles 1702, 1704, along with individual fiberoptic conductor ends 1906 from the third fiberoptic bundle 1706 are arranged in three groups of thirteen optical fibers each: the first group from the first fiberoptic bundle 1702, which transmits light emitted by the blue LED to the aperture 1108; the second group from the second fiberoptic bundle 1704, which transmits light emitted by the amber LED to the aperture 1108; and the third group, which transmits reflected light received at the aperture 1108 through the third fiberoptic bundle 1706 to the photodetector. The thirty-nine fibers (thirteen in each of three groups) each include respective fiberoptic conductor ends 1902, 1904, 1906 arranged in the sigmoidal distribution (or pattern) (see FIG. 19) at the aperture 1108 such that the fiberoptic conductor ends 1902, 1904, 1906 are co-planar at the aperture and in the plane parallel to the plane at the upper surface of the bar code or test strip, when the reader head 706 is positioned to take measurements from the bar code or test strip 100.

At the fiberoptic conductor ends 1902, 1904, 1906, each fiberoptic fiber (or conductor) has a longitudinal axis that is normal to the plane at the upper surface of the bar code or test strip. As a result, light emitted from the fiberoptic conductor ends 1902 and 1904 is directed in a direction substantially normal to this surface plane. The fiberoptic fibers in each of the three groups are arranged along with fiberoptic fibers from the remaining groups in a sigmoidal (or "S"-like) pattern with three columns of thirteen fibers each.

When the immunoassay device is inserted into the cassette slot at the front of the immunoassay reader device 600, the reader head 706 is positioned directly over the bar code or test opening of the assay device such that the longitudinal axes of the optical fibers at their ends 1902, 1904, 1906 at the aperture, are normal to a plane at the surface of the immunoassay test strip and the ends 1902, 1904, 1906 of the fibers at a distance of about 0.010 inches. Light from the first LED and the second LED is transmitted by the fibers onto the bar code or assay test strip at an angle normal to the upper surface of the immunoassay device, and light is reflected normally back from the strip to the ends 1902, 1904, 1906. This reflected light is transmitted by the fibers of the third fiberoptic bundle to the photodetector.

The reader head 706 takes three separate reflectance readings (FIGS. 21, 22 and 23, respectively) from each position at which it reads of the immunoassay test strip. Such measurements are made by reading an output of the photodetector (which is a voltage) while controlling the first and second LED's.

The first reading is used to determine an amount of ambient (or background) light leaking into the immunoassay device (e.g., light leaking through the cassette slot entrance, or light reflected/transmitted into the reader through the housing of the immunoassay device, which may be, for example, white plastic); The first reading is a "dark" reading taken with the blue LED and the amber LED both turned off. This dark reading (which is a voltage at the photodetector) is digitized in a conventional manner using an analog to digital converter, and may be subtracted by the processing unit from other "light" readings made in response to blue LED illumination and amber LED illumination so as to correct for this light leakage.

The second reading, used to determine levels of light reflections associated with the background of the bar code or the assay test strip itself, is taken with the blue LED pulsed on and the amber LED turned off.

The third reading, used to detect the bar code or the presence of the label on the assay test strip is taken with the amber LED pulsed on and the blue LED turned off.

A control circuit (including the processing unit, which includes a processor, such as a microprocessor) receives the digitized output of the photodetector for all three readings, controls the on and off operation of the blue LED and the amber LED, controls when photodetection readings are taken, and controls the position of the reader head 706 by controlling the stepper motor. A memory circuit stores raw and/or processed data (i.e., readings from the photodetector). The data may also be displayed to the operator via the LCD display of the immunoassay reader device 600.

After being positioned above the housing, the reader head 706 is moved (scanned) across the bar code and/or test strip by the stepper motor under the control of the control circuit to allow the reader head 706 to scan the exposed surface of the bar code and/or assay test strip (including the detection and control zones through the test window 214 in the immunoassay device). As stated above, in a preferred embodiment, the distance between reader head 706 and the bar code or assay test strip 100 is approximately 0.010".

The reader head 706 is slidably connected to a rail (e.g., guide rods), and is coupled to a worm or screw gear driven by the stepper motor.

Under the control of the control circuit, the stepper motor drives the reader head 706 along the rail in small steps. At each step, the control circuit takes the three readings described above ("dark", blue LED illuminated, amber LED illuminated). The control circuit moves the reader head 706 such that the fiberoptic conductor ends 1902, 1904, 1906 pass directly above and normal to the exposed surface of the bar code and/or test strip in a sequence of small steps. As explained above, during each step a sequence of "dark", blue LED and amber LED readings are taken and recorded.

The raw data read from the photodetector is then processed by the control circuit to discern the symbology, such as a bar code pattern, in order to provide information regarding the assay device and/or test run and/or reagents, and/or patient with and/or other desired information to read the test strip to determine the presence or concentration of analyte in the sample.

In a preferred embodiment, when reading the test strip, since the detection and control latex stripes are each about 0.020" wide, and since each step of the sensing head is about 0.002" long, there will be about 10 steps within each stripe, i.e., within the test region and the control region. Thus, there will be 10 sets of three readings (i.e., dark, blue LED and amber LED) at the test region and 10 sets of three readings (i.e., dark, blue LED and amber LED) at the control region. The remainder of the reading sets will not be made over either the test region or the control region.

In a preferred embodiment, when the assay device is inserted into the cassette slot of the reader device 600, the reader head 706 is positioned over the bar code or test strip, and the control circuit then moves the head to an initial (or home) position. The control circuit moves (scans) the head across the exposed surface of the bar code or test strip, including the test region and the control region of the strip, in small increments. At each step, the control circuit takes the first reading (FIG. 21) of the photodetector output with the blue LED and the amber LED, both off, takes the second reading (FIG. 22) with the blue LED pulsed on and the amber LED off, and takes a third reading (FIG. 23) with the blue LED off and the amber LED pulsed on. The control circuit then steps the reader head 706 by controlling the stepper motor and repeats the three readings at its new location. For the test strip, this process is repeated for each of 226 steps (0.452" at 0.002"/step) until the surface of the assay test strip is read. Where a bar code is read, the length of the bar code is typically approximately 1 inch in length, and a step size of approximately 0.002–0.008 inch is used; thus between approximately 125–500 steps are performed.

The raw reflectance data are then analyzed by the control circuit in accordance with appropriate software control to identify the symbology, such as a bar code or determine the presence or concentration of the analyte in the sample. Where the reader is used to read a bar code associated with the test device, the data collected from the bar code are transformed into integrated peak information and analyzed as alphanumeric characters to provide information about the assay device and/or test run. Where the reader is used to detect an analyte, the data collected from the test strip are compared to a threshold or reference reflectance value to determine the presence or concentration of the analyte. The output can be displayed via an operator interface, or can be output to another computer or apparatus.

Data Analysis and Decision Support Systems

The systems herein include software for data analysis. Data analysis includes any algorithms or methodology for obtaining diagnostically relevant information from the raw data. Simple algorithms as well as decision-support systems, particularly neural networks are contemplated herein.

In particular embodiments, the data analysis methodology includes, some or all of the following steps: (1) optionally correcting the reflectance readings to correct for light leakage; (2) reducing the raw reflectance data by using a ratiometric formula; (3) generating an image of the test data by plotting the reduced data; (4) expressing this image as a polynomial mathematical function, for example, by using a combination of a flat or parabolic image to represent the baseline and two gaussian curves to represent the peaks; (5) using a curve-fitting algorithm to generate parameters to define the image; (6) optimizing the reconstruction of the image and producing a fitted image; (7) comparing the scanned image and fitted image by solving the linear regression through the curves; (8) validating the parameters obtained from the curve-fitting and the peak heights obtained; and (9) classifying the validated result as positive or negative by comparing peak heights of a clinical sample to reference samples. The method may further include: (10) using the test result with other patient information in a decision-support system to generate a medical diagnosis or risk assessment.

In alternative embodiments, the parameters used to define the image, as in (5) above, and to classify the sample, as in (9) above, can be generated using trained neural networks.

Data Reduction

In an exemplary embodiment, the raw reflectance data obtained from the instrument are stored as an array of points containing a number of rows (n) corresponding to the number of points at which readings were taken along the test strip, and a number of columns (m) corresponding, to the reflectance readings taken at each point, including background or dark readings and readings at different wavelengths. If necessary, the reflectance readings are processed by first subtracting the dark reading taken at the corresponding step to correct for light leakage, which typically is negligible. The corrected reflectance readings are then input into a ratiometric algorithm, which removes noise from the membrane and normalizes data between test strips:

$$f(y)=[(R_{\lambda 1}/R_{max/\lambda 1}*R_{max/\lambda 2}/R_{\lambda 2})].$$

The algorithm is based upon the ratio of readings at the different wavelengths and calculates a reduced data set (1×n), which is used to generate a curve from the original reflectance data. In processing the data, a new column of reduced data is generated by using the ratiometric formula.

When reading an assay test strip, as described above, the size of the matrix is 4×226, where 4 is the number of columns of data collected and 226 is the number of steps, or readings, taken along the test strip. The first column contains information about the location on the test strip from which the data is obtained; the second column is the reflectance in the absence of illumination by the instrument (dark reading); the third column is the reflectance when the test strip is illuminated at the first wavelength (e.g. 430 nm); and the fourth column is the reflectance when test strip is illuminated at the second wavelength (e.g. 595 nm). The information in the second column is usually zero, unless a light breach has occurred with the instrument. The reflectance values in the third and fourth column are preferably in the 3,000–24,000 range.

Where a bar code is read, between approximately 125–500 steps are performed in reading the bar code, therefore, the matrix size would be between 4×125 and 4×500.

In the preferred embodiment described herein, the ratiometric formula would read as follows:

$$f(y)=[(R_{430nm}/R_{max/430nm}*R_{max/595nm}/R_{595nm})]-1.$$

The algorithm calculates a reflectance ratio for each step, generating a fifth column of data. The information contained in the first, third and fourth columns can be converted into an image by plotting the first column α-value) against the fifth column (y-value). Thus, the original data array has been converted to a 2-dimensional image, or an array of the size 1×226. The reflectance ratio is then plotted as a function of each step. In reading an assay test strip, as described above, the result is a two-peak graph with the peaks occurring at the two stripes, corresponding to the detection and control zones. The reflectance data may then be further processed to obtain an accurate determination of analyte concentration in the patient sample.

Where a bar code is read, a graph is produced that corresponds to the reflectance pattern of the bar code. Pattern matching is then performed using any of a number of methods commonly known to those of skill in the art in order to identify the bar code and associate it with the particular assay run.

Generating and Validating Images

The image created by a plot of the data obtained from reading an assay test strip, as described above, has three basic components: a baseline or background that is either flat or parabolic; a peak corresponding to the detection zone that is gaussian; and another peak corresponding to a control zone that is also gaussian.

The parabolic component can be defined using 3 variables:

$$f(y)=Ax^2+Bx+C.$$

Each of the gaussian curves can be defined using 3 variables:

$$f(y)=Area*[exp^{-(x-\mu)(x-\mu)/2\sigma*\sigma}]/(\sigma(2\pi)^{1/2})$$

where
Area=area contained within the gaussian;
$\mu$=x-value of center position; and
$\sigma$=width.

A second plot can be generated from the three component curves, using 9 variables. This process is accomplished using a curve-fit algorithm. Any such algorithm known in the art may be used. Alternatively, the 9 parameters may be obtained using neural networks, as described below. From the parameters generated from the curve-fit function, a showfit function is used to generate an image from the fitted data. For example, in the preferred embodiment, a showfit function is ino used to generate a 1×226 matrix representing the fitted curve defined by the 9 parameters.

The fitted image is then compared to the original scanned image, which is produced by plotting the 1×226 data points as discussed above, to measure the performance of the curve-fit function. This is accomplished by plotting the fitted image against the scanned image and solving the linear regression through these values. The fitted image is then compared to the original image by plotting the fitted image against the scanned image and solving the linear regression through the values, where an exact match would yield a line with slope=1 and $r^2$=1).

Once the curves have been fitted, the peak height of the curve in the detection zone is determined by subtracting the parabolic baseline from the maximum peak height. The peak height is then compared to that of a previously run sample of known analyte concentration. If the peak height of the clinical sample is greater that the peak height of the reference sample, then the test result is positive. If not, a negative test result is returned. The peak height of the curve representing the control zone may also be checked to determine if it meets a required minimum height, in order to test that the system is functioning.

Alternatively, peak areas may be calculated and compared to give a determination of analyte concentration in the sample. The graph may be mathematically analyzed, with a sigmoidal calculation across the background and a gaussian calculation to integrate the area beneath each of the two peaks. The analyte concentration is then determined based upon the ratio of the integrated area beneath each of the two peaks.

Methods for Reducing the Image to Parameters

Images or large sets of data, are not readily amenable for developing and training neural net analyses. For large data sets, the number of inputs required for neural network training must be reduced. To do this assumptions regarding the types of data that can be omitted are made. As a result of the loss of information, the performance of subsequently trained neural nets will hinge on the validity of the assumptions made. A method for reduction of data that reduces dimensionality with minimal or no loss of information will avoid this problem. The reduced database can be validated by using it to reconstruct the original dataset. With minimal or no loss of information, subsequently trained networks should yield higher performance than networks that are trained with less complete data. Methods are provided herein for reducing dimensionality with minimal loss of information. These methods are directly applicable to the images that are generated and data generated from the test strips described herein and is also generally applicable to all images and large datasets.

Methods for Optimizing the Reconstructed Image

Parameters for a mathematical function designed to reproduce; or approximate the scanned image are effective at determining the concentration of the compound being tested and thereby providing a means to classify the sample being tested. Examination of the data, for example, from the fFN test provided herein demonstrates that a scanned image can be constructed from three basic elements. There is a background density, referred to herein as the baseline density. Superimposed on the baseline are the two peaks. The first peak is referred to as the control peak and the second is the test peak. Since the shape of these peaks is very similar to a normal curve, it was assumed that the peaks have a gaussian shape. One characteristic of the "normal curve" that can be exploited is that the area under the curve is always 1.0. By modifying the formula, the height of a peak can be determined from a single function parameter.

When analyzing an image, the peak density function used is:

$$\text{Peak Density} = \text{Height} \cdot \text{EXP}(-Z \cdot Z)$$

where $Z = (X - \text{Pos}) \cdot S$,

X=Pixel Number,

Pos=Pixel number of center of peak,

S=Spread or width of the peak, and

Height=Height of the peak.

This function contains three parameters, Height, S and Pos. When the three parameters are set correctly, this function will closely match one of the peaks in the test strip image. With two peaks in the image, this function can also be used to estimate the second peak. With two peaks, there are six parameters so far that must be optimized. The goal of the optimization will be to change the above parameters in such a way as to reconstruct the image as closely as possible.

In order to reconstruct the image completely, the baseline of the image must also be estimated. Examination of scanned images showed that the baseline had a slight curve. By using a parabolic or quadratic form function, the baseline density is estimated. The function for the base density is, $$\text{Base Density} = X \cdot X \cdot \text{Curve} + X \cdot \text{Slope} + \text{Offset}.$$

Thus, the image can be accurately reconstructed by combining these three function in the following summation, $$\text{Image Density} = \text{Base Density} + \text{Control Peak Density} + \text{Test Peak Density}.$$

This results in a total of nine parameters that must be optimized for an accurate reconstruction of the image.

The basic problem with attempting to fit this complex function to the test strip image is that there are no simple means for finding the optimal values for function parameters as there are for linear regression. There are many numerical techniques that can be used to optimize the parameters of the above image density function. The one used here is the downhill simplex method (see, "Numerical Recipes in C", Second Edition, Cambridge University Press, 1992).

The basic method of this optimization uses an iterative approach to optimize the function parameters based on a defined cost function. Here the cost function is defined as the sum of the squares of the differences between the original image and the reconstructed image for every pixel in the scanned image. The downhill simplex method uses a simplex to accomplish this optimization. A simplex is a geometrical figure in N dimensions containing N+1 points. For the image density function defined above, N has the value 9. In two dimensions, for example, a simplex will contain 3 points, with lines connecting each pair of points. This simplex is called a triangle. As the dimension increases, the complexity of the simplex also increases. In three dimensions a simplex is a tetrahedron. This implies that if there are N parameters to be optimized, then N+1 solutions must be maintained. This translates to $N^2+N$ storage locations that are required to run the algorithm.

For exemplification, the optimization problem with 2 parameters is as follows. The simplex, a triangle, is formed from three points or three different sets of values for the parameters. These three points (call them solutions A, B and C), which are generated in the following way. Starting with and initial set of parameters (solution A), each parameter is perturbed by a small amount (typically 0.01). When the first of the two parameters is changed, solution B is generated. When the second parameter is perturbed, solution C is generated. The three solutions must be evaluated to determine the error function value for each.

Suppose that solution A has the highest error function value. The simplex algorithm attempts to make an improvement by picking a new, point (solution, or set of parameters), that lowers the error function value. This basic operation is called a reflection. Three attempts are made at improving the solution. The first, normal, reflection picks its new set of parameters by forming a line from point A to the average of the remaining points. The line is then extended through the average point an equal distance. This new point is the reflection point. Reflection is the correct term since if one were to place a mirror on the line between B and C, the new point corresponds exactly to the reflection of A in the mirror.

If the new error function value for the normal reflection is better than the best current solution, then an expansion reflection is attempted. In this case the line from A is extended by the Step Up Factor (typically 1.50) through the average point. This operation makes the simplex larger. The point that gave the best error function value (either the normal reflection of A or the Expansion reflection of A) is retained as the new A point.

If the new error function value for the normal reflection is still the worst solution, then a contraction reflection is attempted. In this case the line from A is extended by the Step Down Factor (typically 0.75) through the average point. This operation makes the simplex smaller. If this solution is better than the original error function value for point A, the reflection point is retained as point A. If no improvement is made in the A solution, then the entire simplex is contracted by moving each point toward the point with the best error function value by the fraction specified by the Shrink Factor (typically 0.95). These reflection operations continue until the difference between the best and worst solutions falls below the Restart Tolerance (typically 1.0E-9).

Alternative Method 1 for Reducing the Image to Parameters Using a Neural Network A neural network can be used as an alternative to a polynomial; mathematical function for the purpose of generating parameters that can be used to reconstruct an image. The basic architecture of the neural network contains at least three processing layers. During the training process, a sequence of example images are presented to the network for training. Training continues so that the error between each image and its reconstruction is minimized across the set of images used for training. The image, or a subsection of the image, is presented to the input layer of the network. The middle layer, or hidden layer, of the network contains a number of processing elements that is much smaller than the number of inputs in the input layer. The output layer contains the same number of processing elements as the input layer. The output layer of the network will represent the reconstructed image that is presented to the input layer.

An alternative architecture contains an odd number of hidden layers, with the middle hidden layer containing a much smaller number of processing elements than the input and output layers. In each layer of the network, each processing element is connected to each of the processing element outputs of the previous layer.

The processing element used in the network typically generates a weighted sum of the inputs to processing element, with a transfer function applied to the weighted sum to generate the output of the processing element. The transfer function is any such function normally used in a neural network, including the sigmoid function, or the hyperbolic tangent function.

The neural network can be trained using any standard neural network training rule, including the back propagation learning rule. At each step of the training process, a training image is presented to the inputs of the neural network. The same image is also be presented to the outputs of the network as the desired, or target, output of the network. As learning proceeds, the error between the outputs of the neural network and the desired outputs of the network decreases.

In order for the error to decrease, the neural network middle hidden layer generates a greatly reduced representation of the input image that contains enough information to reconstruct the image. This reduced representation therefore also contains the information needed to classify the image.

Once trained, a new image is presented to the inputs of the neural network. The outputs of the middle hidden layer are then be used as the inputs to the classification means for further processing.

Alternative Method 2 for Reducing the Image to Parameters Using a Neural Network A second alternative method for reducing an image to useful parameters is to substitute the neural network directly in place of the polynomial mathematical function. Here, the inputs of the neural network are the coordinates of the pixel in the image being examined. The desired output of the network are the density value of the associated pixel. The architecture of this neural network is substantially smaller then the architecture described in the first alternative method. Here the weights of the neural network become the parameters to be used by the classifier. The types of processing elements used in this architecture include the radial basis function type, and provisions might be made to allow a mix of processing element types in the hidden layer of the neural network. The architecture is developed to provide the smallest possible number of weights while still being capable of reconstructing the image.

In this alternative, the neural network is trained only on the image under consideration. Thus, each time a sample is tested, the network would be retrained. The weights of the trained network are used as inputs to the classification means.

Validation

Method for Classifying the Image from the Parameters

Once the parameters are estimated, the parameters generated from the image reconstruction process along with several parameters easily calculated from the scanned image are used to classify the sample. In addition, the image parameters from several reference scans were used. The process of classification incorporates two steps. The first is a validation step to determine if the sample under consideration should be rejected or classified. The validated result is then classified as positive or negative as described above.

To ensure the accuracy of a test result, the system producing that result should be validated. Validation protocols are used to confirm that all components of a system operate properly, and that the data received from the system are meaningful. Moreover, in systems where raw data from instruments are manipulated by software, the proper functioning of that software should also be validated.

Validation of data analysis software can be performed in any number of ways. Typically, a known sample (eq reference, positive control, negative control) can be tested in the system to validate that the expected result is obtained. Alternatively, known raw data can be stored in memory and acted upon by the data analysis software to validate that the expected result is obtained. Such validation protocols ensure that the software is operating properly before a clinical sample of interest is evaluated by that system.

Validation of test systems can also be performed during the evaluation of a clinical sample being tested by that system. These types of validation protocols can evaluate components of the system, either individually or together. When the criteria set by validation protocols are not achieved, an invalid result is obtained, and the user will be made aware of the system malfunction. Such processes ensure that only accurate test results are presented to the user.

In an exemplary embodiment, for example, data are validated by several methods. First, the data are checked for completeness by checking that the size of the matrix is m×n, where m is the number of columns of data collected (eq., location on dipstick, dark reading, reflectance at $\lambda_1$ and reflectance at $\lambda_2$) and n is the number of steps, or readings, taken along the test strip. For example, in the preferred embodiment, the matrix must be of an exact size of 4×226.

Next, the maximum peak heights must meet certain minimum values or the test data are invalid. For example, if the sample in question is a fFN positive reference (i.e. about 50 ng/ml of fFN) in the fFN point of care test (POCT), then the maximum control peak height must be between 0.200 and 1.500 units (inclusive) and the maximum test peak height must be between 0.020 and 0.310 units (inclusive) or the result is invalid.

If the sample in question is a fFN POCT positive control, then the maximum test peak height of the positive control (i.e, a control sample that always yields a positive result, typically about 70 to 80 ng/ml for the fFN POCT) must be greater than the maximum test peak height of the positive reference, or the result is invalid.

If the sample in question is a negative control (i.e., always yields a negative result, which for the fFN POCT is about 10–15 ng/ml), then the maximum test peak height of the negative control must be less than the maximum test peak height of the positive reference, or the result is invalid.

A run is only valid when the results of the fFN positive reference, positive control and negative control are all valid.

If the sample in question is a clinical sample, then the maximum control test peak height must be greater than about 0.20 units, or the result for that sample is invalid. Note, however, that the run may remain valid.

For comparison of the fitted image and the scanned image by solving the linear regression, the slope must be between 0.99 and 1.10, or the result is invalid. If the sample is a positive reference, positive control or negative control, then the run is invalid. If the sample is a clinical sample, then the run remains valid. The value of $r^2$ must be greater than 0.78, or the result is invalid. If the sample is a positive reference, positive control or negative control, then the run is invalid. If the sample is a clinical sample, the run remains valid.

For a valid result and valid run, if the maximum peak height of the clinical sample is greater than or equal to the maximum peak height of the positive reference, the test result is positive. If the maximum peak height of the clinical sample is less than the maximum peak height of a negative reference, the result is negative.

Thus, the validated result is then classified as positive or negative as follows:

a) for a valid result and valid run, if maximum peak height of clinical sample is greater than or equal to maximum peak height of fFN positive reference, the result is positive.

b) for a valid result and valid run, if maximum peak height of clinical sample is less than maximum peak height of fFN negative reference, the result is negative.

Alternatively, instead of calculating height, the areas under the curves can be compared. The same data are obtained, if the area under the curve from a clinical sample is compared to the area under the curve of the 50 ng/ml reference sample.

Alternative Method for Classifying the Image Using a Neural Network

Based on the available data generated from scans all possible variables were identified that could be used to improve the ability to classify the sample. The initial training runs used the parameters generated from the image reconstruction process along with several parameters easily calculated from the scanned image. One such parameter is the area under a peak. It can be calculated from original parameters as following:

Area=sqrt($\pi$)*Height/S, where S is spread or width of the peak. A sigma variable, related to the normal distribution can also be calculated from the parameters by:

$$Sigma=1/(sqrt(2)*S).$$

In addition, the image parameters from a Calibrator scan (fFN positive reference) were also used. The following is a list of the variables that are available for use by the neural network.

1. Sample Baseline Square Term
2. Sample Baseline Linear Term
3. Sample Baseline Offset
4. Sample Control Peak Position
5. Sample Control Peak Sigma
6. Sample Control Peak Area
7. Sample Test Peak Position
8. Sample Test Peak Sigma
9. Sample Test Peak Area
10. Sample Test Peak Height
11. Sample Control Peak Height
12. Sample Baseline estimated value between the peaks
13. Sample Ratio of Test Area to Control Area
14. Sample Ratio of Test Height to Control Height
15. Calibrator Baseline Square Term
16. Calibrator Baseline Linear Term
17. Calibrator Baseline Offset
18. Calibrator Control Peak Position
19. Calibrator Control Peak Sigma
20. Calibrator Control Peak Area
21. Calibrator Test Peak Position
22. Calibrator Test Peak Sigma
23. Calibrator Test Peak Area
24. Calibrator Test Peak Height
25. Calibrator Control Peak Height
26. Calibrator Baseline estimated value between the peaks
27. Calibrator Ratio of Test Area to Control Area
28. Calibrator Ratio of Test Height to Control Height.

Four predictor variables were also added. In these variables the calibrator strip value is compared to the sample strip value and a +1 or −1 is used depending on the comparison. The additional variables are:

Test Area Predictor

Area Ratio Predictor

Test Height Predictor

Height Ratio Predictor.

The desired, or target output of the neural network was a classification of the concentration of the sample. If the sample concentration was greater than or equal to 50 ng/ml the desired output was set to 1.0. The desired output was set to 0 otherwise. A sensitivity analysis of the associated training runs was used to indicate which variables were important to the prediction task. The ThinksPro software product from Logical Designs Consulting was used to train the networks and perform the sensitivity analysis. Alternatively, a variable selection process based on genetic algorithms or some other method could be used to select the best subset of variables from this list (see, e.g., copending U.S. application Ser. Nos. 08/798,306 and 08/912,133, which describe a suitable variable selection process).

Using the reduced set of variables one or more networks are trained to estimate the classification of the sample. If more than one network is used, the outputs of each network are averaged together to give a consensus result.

In another embodiment, the nine variables may optionally be fed through a previously trained neural network to obtain a test result. For example, the nets may be trained with data for which ELISA test results are known. Alternatively, variables other than the nine described above may be used to train the neural net. The nets can be used not only to return positive or negative results, but also to determine if the assay itself is valid for any particular run.

The reduction of data for input to neural networks can be accomplished by a neural network itself. An example of such a net is a net with an hourglass architecture with an input, output and three hidden layers, wherein the input and output layers contain n nodes, with the first and third hidden layers containing less than n nodes, and the second hidden layer containing five nodes. If trained so that the output layer exactly matches the input layer, such nets would reduce the original dataset of n elements down to five elements, and also retain the ability to reconstruct the original dataset of n elements from these five elements.

Further Analysis Using Decision Support Systems

The output from the data analysis step provides an assessment of the raw biochemical test data that is measured by the reader or other instrument. Such data may then be considered as is but they can be further entered into a decision-support system, particularly a neural network, that has been trained to evaluate the particular data and disease. For example, U.S. application Ser. No. 08/599,275, now abandoned, copending U.S. application Ser. No. 08/798,306, and copending U.S. application Ser. No. 08/912,133, filed Aug. 14, 1997, as well as published International PCT application No. WO 97/29447, which claims priority to U.S. application Ser. No. 08/599,275, filed Feb. 9, 1996, now abandoned, and copending U.S. application Ser. No. 08/798, 306 and corresponds to U.S. application Ser. No. 08/912,133 describe neural nets and methods for developing neural networks for diagnosis of disorders. The accuracy of biochemical test data is improved when used in these neural nets. Such neural nets, are thus contemplated for inclusion in the systems herein.

Briefly, in the methods described in these applications patient data or information, typically patient history or clinical data, are analyzed by the decision-support systems to identify important or relevant variables and decision-support systems are trained on the patient data. Patient data are augmented by biochemical test data or results to refine performance. The resulting decision-support systems are employed to evaluate specific observation values and test data to guide the development of biochemical or other diagnostic tests, to assess a course of treatment, to identify new diagnostic tests and disease markers, to identify useful therapies, and to provide the decision-support functionality for the test. Methods for identification of important input variables for a medical diagnostic test for use in training the decision-support systems to guide the development of the tests, for improving the sensitivity and specificity of such tests, and for selecting diagnostic tests that improve overall diagnosis of, or potential for, a disease state and that permit the effectiveness of a selected therapeutic protocol to be assessed are also provided. The methods for identification can be applied in any field in which statistics are used to determine outcomes. A method for evaluating the effectiveness of any given diagnostic test is also provided.

Thus, such neural networks or other decision-support systems will be included in the systems provided herein as a means of improving performance of the biochemical test data.

The following examples are included for illustrative purposes only and are not intended to limit the scope of the invention.

EXAMPLE 1

Immunoassay Test Strip

A. The Test Strip

The test strip 100 includes a membrane system including three components: a porous or bibulous member 102; a conjugate pad 108; and an absorbent pad 110. The membrane system may be mounted on a substrate or backing 112, with the conjugate pad 108 and the absorbent pad 110 slightly overlapping the porous or bibulous member 102, which is interposed thereinbetween. As can be seen in FIGS. 1A and 1B, the conjugate pad 108 overlaps the porous or bibulous member 102 so that a fluid sample placed onto the conjugate pad 108 is communicated from the conjugate pad 108 to the porous or bibulous member 102. Similarly, the absorbent pad 110 overlaps with the porous or bibulous member 102 so that fluid samples introduced into the porous or bibulous member 102 from the conjugate pad 108 can then be transmitted to the absorbent pad 110. Thus, the conjugate pad 108, the absorbent pad 110 and the porous or bibulous member 102 are all in fluid communication with one another, making any fluid sample placed on the conjugate pad 108 able to propagate through the conjugate pad 108 to the porous or bibulous member 102 and then to the absorbent pad 110.

The porous or bibulous member is capable of transporting a liquid sample along the test strip and serves as the solid support upon which the immunoreactions occur. Antibodies which react with the target analyte and/or label are immobilized on the solid support. Possible solid supports include paper and cellulose derivatives, such as cellulose esters and ethers, natural and synthetic polymeric materials, such as vinyl polymers and partially hydrolyzed derivatives, polycondensates, copolymers and inorganic materials. A preferred solid support is a nitrocellulose membrane.

The porous or bibulous member contains two distinct zones, a detection zone 104 and a control zone 106, at which two different antibodies are immobilized. The detection zone contains an immobilized capture antibody that binds the analyte of interest, whereas the control zone contains an immobilized antibody or other component, such as an antigen, that binds labeled antibody conjugate (discussed below) which has not bound with the analyte.

The membrane system also includes a conjugate pad 108, which serves as a sample application component, and which includes an antibody to the analyte, which is conjugated to a detectable label. The conjugate pad is in fluid communication with the porous or bibulous member 102. The labeled antibody conjugate is diffusively bound to the conjugate pad and becomes mobile upon application of the liquid sample and moves along the test strip. The conjugate pad is made of a porous material, such as glass fiber. The conjugate pad may also act as a pre-filter for the sample.

The membrane system may also include an absorbent pad 110, which is also in fluid communication with the porous or bibulous member, and which serves to draw liquid continuously through the device. The absorbent strip may be made of a material such as cellulose paper or other material known to those of skill in the art.

Referring to FIG. 2A, which depicts an exemplary immunoassay device, including a test strip and housing assembly 200, the housing 202 generally surrounds the test strip 100 (FIGS. 1A and 1B) and includes an opening through which test sample is applied 204, as well as an aperture above the detection and control zones 206 that permits measurement of the amount of label by the reader, which is correlated with the amount of analyte in the test sample. The housing 202 includes at its upper surface 208 a fattened end 210, used for gripping the housing 202, an application window 204 (or sample window) through which a sample is applied to a conjugate pad 108 of an immunoassay test strip within the housing 202. The housing 202 also includes a test window 214 through which the test result of the immunoassay is viewed. In accordance with the embodiments shown, no window material is mounted within the test window 214 (or the sample window 212). Thus, an optical path from outside the housing 202 through the test window 214 to the immunoassay test strip is unobscured by even a transparent material. Other alternative embodiments may include an optically transparent material (transparent at wavelengths emitted by light emitted from devices described herein), however, such is not preferred. Also, as shown in FIG. 2A and FIG. 2B, the housing may include a symbology, exemplified as a bar code 216 or 316 that can be read by the reader or a separate reading device and associated with identifying information pertaining to the particular device and/or test run or other information.

An alternative embodiment of the test device is shown in FIG. 2B. The components of device are shown in FIG. 3 and include the upper and lower members 302 and 304 of the housing and the test strip 100. Also shown are the sample application port 306, test window 308, and the optionally included bar code 316. Also shown are an aperture 306 above the detection and control zones, the upper surface 308 of upper member 302, an end 310 used for gripping the housing, and a sample window 312.

Referring next to FIG. 4 a top view is shown of the immunoassay test strip housing 202 of FIG. 2A. Shown are the sample window 212, and the test window 214, and the enlarged gripping portion 210. Also shown are structures 402 for holding the immunoassay test assembly within the housing 202 and structures 404 for securing upper and lower halves of the housing 202 to one another.

Referring next to FIG. 5, a side cross-sectional assembly view is shown of the housing 202 for the immunoassay test strip 100. Shown are the sample window 212, the test window 214, and the structures 402 for holding the immunoassay test strip assembly in place within the housing 202. As can be seen, an upper half 502 of the housing 202 is mated with a lower half 504 of the housing 202. The immunoassay test strip is sandwiched between the upper and lower halves 502 and 504 of the housing 202 and is secured in place by the structures 402 of the upper half 502. The immunoassay test strip is positioned so as to be viewable through the test window 214 when the immunoassay test strip assembly is secured within the housing and the conjugate pad is positioned to be contactable through the sample window 212.

These devices are particularly adapted for use with the reflectance reader provided herein.

B. Colored Latex Label

The immunoassay test strip includes a membrane system supported on a plastic backing. The membrane system is formed from three partially overlapping materials: a conjugate pad made of Whatman glass fiber (F075-07S, 2.4 cm length) treated with polyvinyl alcohol (PVA), a nitrocellulose strip supplied by Sartorius (8 $\mu$m, 3.3 cm length) and an absorbent pad made of Whatman C7218 (1.65 cm length) cellulose paper. These three materials are in fluid communication with each other. The conjugate pad and nitrocellulose overlap by 1 mm; the nitrocellulose and absorbent pad overlap by 4 mm. The membrane materials are hand-laminated and attached to a membrane card, which is cut using an Azco guillotine compression cutter, using G&L adhesive membrane.

The conjugate pad contains a mouse monoclonal anti-fFN antibody (FDC-6 or A137) conjugated to latex particles containing a blue dye. The conjugate pad acts as a pre-filter for the sample in that mucous from the sample is left behind in the conjugate pad after performing the assay.

The latex particles, which are polymerized from styrene and acrylic acid, may be any suitable latex particles (such as are available from Bangs Laboratories). The particles are polymerized in an aqueous solution with a surfactant added. The particles are internally labeled with blue dye by swelling the particles in organic solvent and adding the dye. The particles are then placed in an aqueous solvent, which shrinks the particles and traps the dye. The dye is an organic soluble blue dye. Carboxyl groups are covalently attached to the surface of the bead for coupling to the antibody. The particles are supplied as a 2.5–10% aqueous suspension containing surfactant as Bangs Uniform Microsphere Stock D0004031CB and have a mean diameter of 0.40 $\mu$m, with a standard deviation of 0.4 $\mu$m, and a surface area of 1.405e+13 $\mu$m$^2$/g.

Antibodies are conjugated to the latex particles in a one-step covalent conjugation process using EDAC, a carbodiimide coupling reagent. The conjugate is characterized as 1% solids; 50 $\mu$g/mg beads total bound protein (Bead BCA); and >80% covalent bound protein (Tris-SDS+Bead BCA).

The antibody conjugated to the latex particles is mouse monoclonal antibody specific for fetal fibronectin. The antibody (FDC-6 or A137 monoclonal) is raised against whole molecule onco-fetal fibronectin from a tumor cell line. The antibody is produced as ascites at a contract manufacturer and is purified by Protein G and dialyzed into PBS buffer.

The nitrocellulose strip contains two distinct zones, a detection zone and a control zone; at which two different antibodies are immobilized. The detection zone contains immobilized anti-fibronectin polyclonal antibody as a capture antibody, whereas the control zone contains immobilized goat anti-mouse polyclonal antibody. The anti-fibronectin polyclonal antibody is produced in goats. The antisera is obtained from a commercial source and is purified by use of a fibronectin column which is made by attaching purified fibronectin (antigen) to a resin. The antisera is passed through a column containing the resin. After washing unbound material, the antibody is eluted via low pH glycine. The purified antibody is then dialyzed. The goat anti-mouse IgG antibody (GAMGG) immobilized in the control zone is obtained from Biosource. The antibody is purified by passing the serum through a mouse IgG column, which binds the antibody, and then eluting off the antibody using glycine.

The antibodies are applied to the conjugate pad and nitrocellulose strip using an IVEK Linear Striper, which is a volumetric ceramic piston pump dispenser. The anti-fibronectin polyclonal capture antibody is applied in a 1×Spotting Buffer P/N 00387, which contains citrate, phosphate and NaCl, at an antibody concentration of 1 mg/ml and a striping rate of 1 $\mu$l/sec. The position of the test line is 37–40 mm from the bottom of the strip. The control antibody is applied in a 1×Spotting Buffer P/N 00387 at a concentration of 0.5 mg/ml and a striping rate of 1 $\mu$l/sec. The position of the control line is 43–46 mm from the bottom of the strip. The dimensions of the antibody stripes are approximately 7.5 mm (wide)×0.5–1.0 mm (high). The nitrocellulose strip is not otherwise treated after application of the capture and control antibodies to block non-specific binding sites.

The detection and control stripes are applied to the strip and then dried for 60 minutes at RT, after which the conjugate is striped onto the strip. The conjugate is mixed in a diluent containing 20% sucrose, 0.2% BSA, 0.5% TW20 and 100 mm Tris. After application of the conjugate, in the strip is then dried for 30 min. at 37° C.

The test strip is contained within a housing, which includes a lower member and an upper member with openings that include a circular aperture above the area of the conjugate pad, through which test sample is applied, and a rectilinear aperture above the detection and control zones. The circular application aperture is in contact with the test strip. The latex conjugate is placed slightly downstream from the sample application opening. The upper and lower members are mated together to sandwich the test strip. The test strip is confined non-removably in the housing, and the device is not intended to be re-usable. The upper member is configured for use with a reader that measures the amount of label that is indicative of the amount of fetal fibronectin in the test sample.

C. Colloidal Gold Label

In an alternative embodiment, colloidal gold is used for labeling the antibody. The test strip configuration is similar to that described in EXAMPLE 1A for the latex particle embodiment, with the following modifications.

In the colloidal gold assay, a goat polyclonal antibody to human adult and fetal fibronectin is present in the conjugate pad, immobilized mouse monoclonal anti-fetal fibronectin antibody (specific to the III CS region of fetal fibronectin) is present in the detection zone of the nitrocellulose test strip and immobilized human adult fibronectin is present in the control zone.

The anti-fibronectin antibodies (polyclonal) are labeled with colloidal gold by passively adsorbing anti-fibronectin antibodies onto colloidal gold. This preparation is then treated with a solution containing protein and polyvinyl pyrrolidone (PVP) to coat the colloidal gold particles. This method is described in Geoghegan and Ackerman, *Journal of Histochemistry and Cytochemistry*, 25(11):1187–1200 (1977).

EXAMPLE 2

Immunoassay Procedure

A. Colored Latex Label

In conducting the assay, the sample is extracted from a swab into antiprotease transfer buffer (0.05 M Tris buffer, pH 7.4, 1% BSA, 5 mM EDTA, 1 mM phenylmethylsulfonyl fluoride (PMSF), and 500 Kallikrein Units/ml of Aprotinin), heated for 15 min. at 37° C. and filtered through a large pore (25$\mu$) plunger filter. A volume of 200 $\mu$l of test sample is then delivered to the conjugate pad at the application zone using a standard plastic pipet. Any fFN in the sample will bind to the labeled monoclonal antibody and the resulting complex migrates into the nitrocellulose strip. When the complex encounters the detection zone, the immobilized anti-FN antibody binds the complex, thereby forming a colored stripe due to the aggregation of the dye-containing latex beads. Any unbound latex-conjugated anti-fFN antibody continues to migrate into the control zone, where it is captured by the immobilized goat anti-mouse antibody and thereby forms a colored stripe due to the aggregation of the dye-containing latex beads. The reaction time is 20 minutes.

B. Colloidal Gold Label

The test strip assay procedure is similar to that described in EXAMPLE 2A for the latex particle embodiment, with the following modifications. The buffer used to extract the sample is Tris-acetate and a protein matrix (4% PSA and 4% PVP).

Fetal fibronectin and adult human fibronectin in the sample bind with the labeled anti-fibronectin antibody conjugate on the conjugate pad. The labeled fetal fibronectin-anti-fibronectin complex and adult human fibronectin-anti-fibronectin complexes, and unbound labeled anti-fibronectin conjugate migrate into the nitrocellulose strip, where they encounter the detection region, including immobilized anti-fetal fibronectin monoclonal antibody.

In the detection region, the immobilized anti-fetal fibronectin capture antibody binds with the fetal fibronectin-anti-fibronectin complex, whereby a gold label forms a colored stripe with the to concentration of the gold label. The amount of gold label bound to the test region correlates with the amount of fetal fibronectin in the sample.

The unbound labeled anti-fibronectin antibody conjugate and adult human fibronectin-anti-fibronectin complex then pass to the control region of the immunoassay test strip, which includes immobilized adult human fibronectin. There, any unbound antibody conjugate binds to the immobilized adult human fibronectin, where the gold label forms a second colored stripe. The presence of a colored stripe indicates that the assay results are valid, whereas the absence of this stripe indicates that the results are not valid, i.e., that the sample did not reach the control region, and thus a good reading at the test region cannot be assumed. Any adult human fibronectin-anti-fibronectin complexes formed do not bind with the detection or control zones.

EXAMPLE 3

Operation of the Reflectance Reader

The test strip is read using the reflectance reader exemplified herein. This reader (described above) is adapted to read an immunochromatographic test strip supported within the housing. The reflectance reader includes a cassette slot for receiving the test-strip housing, and a sensing head assembly for reading the test strip supported within the test-strip housing using reflected light. The sensing head assembly includes a first light-emitting diode ($LED_1$), a second LED ($LED_2$), a silicon photodiode detector, and 39 optical fibers randomly arranged in a narrow slit (e.g., 0.020" wide) located at the bottom of the sensing head assembly. LED, emits light with a wavelength of 430 nm (blue), and $LED_2$ emits light with a wavelength of 595 nm (amber). The optical fibers are arranged in three groups of 13 optical fibers each: the first group transmits light emitted by $LED_1$ to the slit; the second group transmits light emitted by $LED_2$ to the slit; and the third group transmits reflected light received at the slit to the photodetector. The 39 fibers each include an end randomly arranged within a plane located at the slit such that the ends are co-planar, with the plane being normal to the test strip when the sensing head assembly is positioned (as described below) to take reflectance readings. The optical fibers in each of the three groups are randomly arranged within the plane with respect to the fibers of the other two groups.

The slit width is selected to be as narrow as permitted, with the practical minimum being driven by the availability of small diameter optical fibers. The maximum slit width should not be larger than about 90% of the width of the colored stripe, otherwise the background of the strip, in addition to the colored stripe, will be read and less color will be detected, unless the slit, or aperture, is positioned directly above the colored stripe.

When the housing is inserted into the cassette slot of the reader, a spring mechanism rotates the sensing head directly over the second aperture of the housing such that the plane defined by the optical fibers is normal to the surface of the nitrocellulose strip at a distance of about 0.010". Light from $LED_1$ and $LED_2$ can be transmitted by the fibers onto the nitrocellulose strip at a normal angle, and light reflected normally from the strip can be transmitted by the fibers to the photodetector.

The sensing head takes three separate reflectance readings of each portion of the nitrocellulose strip by reading the output of the photosensor while controlling $LED_1$ and $LED_2$. The first reading, used to determine the amount of ambient light leaking into the reader (e.g., light leaking through the slot entrance, or light reflected into the reader through the white plastic of the housing), is a dark reading taken with $LED_1$ and $LED_2$ both turned off. The dark reading count is subtracted from the other two readings to correct for light leakage. The second reading, used to determine background reflections associated with the nitrocellulose, is taken with LED, pulsed on and $LED_2$ turned off. The third reading, used to detect the presence of the latex label on the test strip, is taken with $LED_2$ pulsed on and LED, turned off. A control circuit reads the photodetector output and controls the on and off operation of $LED_1$ and $LED_2$. A memory circuit stores the raw and/or processed data. The data may also be displayed to the operator via an appropriate interface (e.g., an alphanumeric character matrix).

After being positioned above the housing by the spring mechanism, the sensing head can be moved slidably across the test strip to allow the head to scan the entire exposed surface of the nitrocellulose strip (including the detection and control zones). In the preferred embodiment, this distance is approximately 0.452". The head is slidably connected to a rail (e.g., guide rods), and is coupled to a worm or screw gear driven by a stepper motor. Under the control of the control circuit, the stepper motor drives the head along the rail in small steps (e.g., 0.002"/step). At each step, the control circuit takes three readings as described above. Thus, the control circuit moves the head such that the optical fibers pass directly above and normal to the exposed surface of the nitrocellulose strip in a sequence of small steps, and takes a sequence of dark, LED, and $LED_2$ readings at each step. The control circuit then processes the data read from the photodetector at each sequence of three readings to determine the presence or concentration of fFN.

Since the detection and control latex stripes are each about 0.020" wide, and since each step of the sensing head is about 0.002" long, there will be about 10 steps within each stripe. Thus, there will be 10 sets of three readings (i.e., dark, $LED_1$ and $LED_2$) at each of the stripes, and the remainder of the reading sets will not be made over either stripe.

The control circuit processes the $LED_1$ and $LED_2$ readings by first subtracting the "dark reading" taken at the corresponding step to correct for light leakage. The corrected $LED_1$ and $LED_2$ readings are then input into a ratiometric algorithm to determine the concentration of fFN. The algorithm is based upon the ratio of readings at the detection and control zones. If a sample includes a high concentration of fFN, latex readings at the detection zone will be relatively high and the readings at the control zone will be low. If the sample includes a low concentration of fFN, however, latex readings at the detection zone will be relatively low and readings at the control zone will be high. The algorithm calculates a reflectance ratio for each step which equals (amber count−dark count)/(blue count−dark count). Generally, light leakage is so minimal that this step can be omitted. If the reflectance ratio is graphed as a function of the steps, the result will be a two-peak graph with the peaks occurring at the two stripes. The graph is mathematically analyzed, with a sigmoidal calculation across the background and a gaussian calculation to integrate the area beneath each of the two peaks. The fFN concentration is then determined based upon the ratio of the integrated area beneath each of the two peaks.

In operation, when the test-strip housing is inserted into the cassette slot of the reader, the sensing head rotates down over the exposed nitrocellulose strip, and the control circuit then moves the head to an initial position. The control circuit moves the head across the exposed surface of the nitrocellulose strip, including the detection and control zones, in small increments of 0.002" each. At each step, the control circuit takes a first reading of the photodetector output with LED, and $LED_2$ both off, takes a second reading with $LED_1$ pulsed on and $LED_2$ off, and takes a third reading with LED, off and $LED_2$ pulsed on. The control circuit then steps the sensing head and repeats the three readings. This process is repeated for each of 226 steps (0.452" at 0.002"/step) until the entire surface is read. The control circuit may then analyze the raw data to determine the presence or concentration of fFN. The output values can be displayed via an operator interface, or can be outputted to another computer or apparatus.

Since modifications will be apparent to those of skill in this art, it is intended that this invention be limited only by the scope of the appended claims.

What is claimed is:

1. A method for reading a surface of a test strip comprising an image, comprising:

moving a reader head in a reflectance reader to a first position over the surface comprising the image;

measuring a first amount of light reflected from the surface comprising the image;

uniformly illuminating the surface with light of a first wavelength, and measuring a second amount of light reflected from the surface; and uniformly illuminating the surface with light of a second wavelength, and measuring a third amount of light reflected from the surface, wherein the reader head comprises:

a reader head body;

a light emitting diode;

a first fiberoptic bundle optically coupled to the light emitting diode;

a photodetector;

a second fiberoptic bundle optically coupled to the photodetector;

an aperture in the reader head body; and a plurality of fiberoptic conductor ends arranged in a sigmoidal distribution in the aperture, wherein: a first portion of the fiberoptic conductor ends comprises fiberoptic conductors of the first fiberoptic bundle; and a second portion of the fiberoptic conductor ends comprises fiberoptic conductors of the second fiberoptic bundle.

2. The method of the claim 1, wherein the reflectance reader further comprises, a control unit including a processor modified with a software subsystem, wherein the software subsystem is for analyzing data produced in the steps of determining the first, second and third amounts of light reflected from the surface.

3. The method of claim 1, further comprising performing an immunoassay on the test strip.

4. A method for reading a surface of a test strip comprising an image, comprising:

moving a reader head in a reflectance reader to a first position over the surface comprising the image;

measuring a first amount of light reflected from the surface comprising the image;

uniformly illuminating the surface with light of a first wavelength, and measuring a second amount of light reflected from the surface; and uniformly illuminating the surface with light of a second wavelength, and measuring a third amount of light reflected from the surface, wherein the reflectance reader comprises:

the reader head comprising:
  a reader head body;
  a light emitting diode;
  a first fiberoptic bundle optically coupled to the light emitting diode, and adapted to transmit light from the light emitting diode;
  a photodetector adapted for generating a reflection signal in response to reflected light;
  a second fiberoptic bundle optically coupled to the photodetector, and adapted to transmit an amount of reflected light to the photodetector;
  an aperture in the reader head body; and
  a plurality of fiberoptic conductor ends arranged in a sigmoidal distribution in the aperture, wherein: a first portion of the fiberoptic conductor ends comprises fiberoptic conductors of the first fiberoptic bundle; and a second portion of the fiberoptic conductor ends comprises fiberoptic conductors of the second fiberoptic bundle, the plurality of fiberoptic conductor ends being further arranged in a substantially co-planar relationship;

and a reader housing comprising:
  a housing body; and
  a cassette slot adapted to receive a test device.

5. The method of the claim 4, wherein the reflectance reader further comprises, a control unit including a processor modified with a software subsystem, wherein the software subsystem is for analyzing data produced from the steps of determining the first, second and third amounts of light reflected from the surface.

6. The method of claim 4, further comprising performing an immunoassay on the test strip.

7. The method of claim 1, further comprising determining a parameter correlated with the intensity or shape of the image, wherein the parameter is the amount of an analyte in a sample, which is a function of the first amount of light reflected, the second amount of light reflected, and the third amount of light reflected.

8. The method of claim 1, wherein the method further comprises determining an amount of an analyte in a sample by correlating a parameter with the amount of analyte in the sample.

9. The method of claim 1, wherein said first wavelength is selected to reflect equally from all regions of the test strip, whereby said second amount of light is indicative of a test region of the test strip.

10. The method of claim 1, wherein said second wavelength reflects from a test region of the test strip, whereby said third amount of light is indicative of an amount of a label at the test region.

11. The method of claim 1, further comprising determining an amount of an analyte in a sample, wherein the analyte is fetal fibronectin.

12. The method of claim 4, further comprising determining an amount of an analyte in a sample, wherein the analyte is fetal fibronectin.

13. The method of claim 1, wherein the image comprises a stripe on the surface of the test strip.

14. The method of claim 1, further comprising:
  determining a parameter correlated with an intensity or shape of the image.

15. A method for reading a surface of a test strip comprising an image, comprising:
  moving a reader head in a reflectance reader to a first position over the surface comprising the image;
  measuring a first amount of light reflected from the surface comprising the image;
  uniformly illuminating the surface with light of a first wavelength, and measuring a second amount of light reflected from the surface;
  uniformly illuminating the surface with light of a second wavelength, and measuring a third amount of light reflected from the surface;
  moving the reader head to a second position over the surface comprising the image;
  measuring a fourth amount of light reflected from the second position on the surface comprising the image;
  uniformly illuminating the second position on the surface with light of the first wavelength, and measuring a fifth amount of light reflected from the surface;
  uniformly illuminating the second position on the surface with light of the second wavelength, and measuring a sixth amount of light reflected from the surface; and
  determining a parameter correlated with an intensity or shape of the image.

16. A method for reading a surface of a test strip comprising an image, comprising:
  (a) moving a reader head in a reflectance reader to a first position over the surface comprising the image;
  (b) measuring a first amount of light reflected from the surface comprising the image;
  (c) uniformly illuminating the surface with light of a first wavelength, and measuring a second amount of light reflected from the surface;
  (d) uniformly illuminating the surface with light of a second wavelength, and measuring a third amount of light reflected from the surface;
  (e) repeating each of steps (b) through (d) at additional positions on the surface until the image on the surface of the test strip is scanned; and
  (f) determining an intensity or shape of the image.

17. A method for reading a surface of a test strip comprising an image, comprising:
  moving a reader head in a reflectance reader to a first position over the surface comprising the image;
  measuring a first amount of light reflected from the surface comprising the image;
  transmitting light of a first wavelength onto the surface at an angle normal to the surface, and measuring a second amount of light reflected normally from the surface; and
  transmitting light of a second wavelength onto the surface at an angle normal to the surface, and measuring a third amount of light reflected normally from the surface.

18. A method for reading a surface of a test strip comprising an image, comprising:
  with a reader head in a reflectance reader at a first position over the surface comprising the image, measuring a first amount of light reflected from the first position of the surface comprising the image;
  transmitting light of a first wavelength onto the first position of the surface at an angle normal to the surface, and measuring a second amount of light reflected normally from the surface;
  transmitting light of a second wavelength onto the first position of the surface at an angle normal to the surface, and measuring a third amount of light reflected normally from the surface;
  moving the reader head to a second position over the surface comprising the image;
  measuring a fourth amount of light reflected from the second position on the surface comprising the image;
  transmitting light of the first wavelength onto the second position of the surface at an angle normal to the surface, and measuring a fifth amount of light reflected normally from the surface;

transmitting light of the second wavelength onto the second position of the surface at an angle normal to the surface, and measuring a sixth amount of light reflected normally from the surface; and determining a parameter correlated with an intensity or shape of the image.

19. A method for reading a surface of a test strip comprising an image, comprising:

(a) moving a reader head in a reflectance reader to a first position over the surface comprising the image;

(b) measuring a first amount of light reflected from the surface comprising the image;

(c) uniformly illuminating the surface with light of a first wavelength, and measuring a second amount of light reflected from the surface;

(d) uniformly illuminating the surface with light of a second wavelength, and measuring a third amount of light reflected from the surface; and (e) moving the reader head in a stepwise fashion to a plurality of positions over the test strip, wherein steps (b) through (d) are repeated at each of the plurality of positions to determine an intensity or shape of the image.

20. The method of claim 1, wherein the step of measuring a first amount of light is carried out while no light is produced by a light source in the reader head.

21. The method of claim 1, wherein the first wavelength is blue.

22. The method of claim 1, wherein the second wavelength is amber.

23. The method of claim 1, wherein the measuring the first amount of light is used to determine an amount of background light.

24. The method of claim 1, wherein the measuring the second amount of light is used to determine levels of light reflections associated with the background of the bar code or the assay test strip.

25. The method of claim 1, wherein the measuring the third amount of light is used to detect a symbology or the presence of an analyte on the test strip.

26. The method of claim 1, further comprising one or more steps selected from the group consisting of: (1) using the light measurements to correct for light leakage; (2) reducing the light measurements using a ratiometric formula; (3) reducing the light measurements using a neural network; (4) creating a generated image of test data by plotting reduced light measurements; (5) expressing a generated image as a polynomial mathematical function; (6) using a curve-fitting algorithm to generate parameters to define a generated image; (7) optimizing a reconstruction of a generated image and producing a fitted image; (8) comparing light measurements and fitted image by solving the linear regression; (9) validating one or more parameters obtained from linear regression and one or more peak heights obtained; (10) classifying a validated result as positive or negative by comparing peak heights of a clinical sample to reference samples; (11) classifying a result using a neural network; and (12) using a test result with other patient information in a decision-support system to generate a medical diagnosis or risk assessment.

27. A method for reading a surface of a test strip comprising an image, comprising:

moving a reader head in a reflectance reader to a first position over the surface comprising the image;

measuring a first amount of light reflected from the surface comprising the image;

uniformly illuminating the surface with light of a first wavelength, and measuring a second amount of light reflected from the surface;

uniformly illuminating the surface with light of a second wavelength, and measuring a third amount of light reflected from the surface; and emitting the light of the first wavelength from a light emitting diode;

transmitting the emitted light of the first wavelength through a first fiberoptic bundle to the surface of the test strip; and transmitting the second amount of light reflected from the surface of the test strip through a second fiberoptic bundle to a photodetector.

28. A method for reading a surface of a test strip comprising an image, comprising:

moving a reader head in a reflectance reader to a first position over the surface comprising the image;

measuring a first amount of light reflected from the surface comprising the image;

uniformly illuminating the surface with light of a first wavelength, and measuring a second amount of light reflected from the surface;

uniformly illuminating the surface with light of a second wavelength, and measuring a third amount of light reflected from the surface; and emitting the light of the first wavelength from a first light emitting diode;

transmitting the emitted light of the first wavelength through a first fiberoptic bundle to the surface of the test strip;

transmitting the second amount of light reflected from the surface of the test strip through a second fiberoptic bundle to a photodetector;

emitting the light of the second wavelength from a second light emitting diode;

transmitting the emitted light of the second wavelength through a third fiberoptic bundle to the surface of the test strip; and transmitting the third amount of light reflected from the surface of the test strip through the second fiberoptic bundle to the photodetector.

29. The method of claim 1, wherein the reader head further comprises a second light emitting diode and a third fiberoptic bundle optically coupled to the second light emitting diode;

wherein the plurality of fiberoptic conductor ends arranged in a sigmoidal distribution in the aperture further comprises a third portion of fiberoptic conductor ends comprising fiberoptic conductors of the third fiberoptic bundle.

30. The method of claim 4, wherein the reader head further comprises a second light emitting diode and a third fiberoptic bundle optically coupled to the second light emitting diode;

wherein the plurality of fiberoptic conductor ends arranged in a sigmoidal distribution in the aperture further comprises a third portion of fiberoptic conductor ends comprising fiberoptic conductors of the third fiberoptic bundle.

* * * * *

UNITED STATES PATENT AND TRADEMARK OFFICE
CERTIFICATE OF CORRECTION

PATENT NO. : 6,867,051 B1
DATED : March 15, 2005
INVENTOR(S) : Anderson et al.

It is certified that error appears in the above-identified patent and that said Letters Patent is hereby corrected as shown below:

Title page,
Item [73], Assignee, please replace "Adeza Biomedical, Inc." with -- Adeza Biomedical Corporation. --.
Item [56], References Cited, FOREIGN PATENT DOCUMENTS, please list -- WO 99/39298 --.

Signed and Sealed this

Eighth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,867,051 B1  Page 1 of 1
APPLICATION NO. : 09/717478
DATED : March 15, 2005
INVENTOR(S) : Anderson et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (20) days Delete the phrase "by 20 days" and insert -- by 140 days--

Signed and Sealed this

Twenty-sixth Day of June, 2007

JON W. DUDAS
*Director of the United States Patent and Trademark Office*